(12) United States Patent
Seemayer et al.

(10) Patent No.: US 6,734,313 B2
(45) Date of Patent: May 11, 2004

(54) SYNTHESIS OF SPIRO ESTERS, SPIRO ORTHO CARBONATES, AND INTERMEDIATES

(75) Inventors: Robert Seemayer, Belmont, CA (US); Jack Liang, Mountain View, CA (US)

(73) Assignee: Bioavailability Systems, LLC, Cocoa Beach, FL (US)

( * ) Notice: Subject to any disclaimer, the term of this patent is extended or adjusted under 35 U.S.C. 154(b) by 0 days.

(21) Appl. No.: 10/434,361

(22) Filed: May 9, 2003

(65) Prior Publication Data

US 2004/0002611 A1 Jan. 1, 2004

Related U.S. Application Data

(63) Continuation of application No. 09/982,827, filed on Oct. 22, 2001, now Pat. No. 6,613,918.
(60) Provisional application No. 60/241,850, filed on Oct. 20, 2000.

(51) Int. Cl.[7] ............................................. C07D 493/00
(52) U.S. Cl. ..................... 549/282; 549/289; 549/334; 568/591; 568/592; 568/595
(58) Field of Search ................................. 549/282, 289, 549/334; 568/591, 592, 595

(56) References Cited

U.S. PATENT DOCUMENTS

| | | | |
|---|---|---|---|
| 4,217,445 A | 8/1980 | Nikolaiski | 536/4 |
| 4,387,215 A | 6/1983 | Bailey | 528/354 |
| 4,738,899 A | 4/1988 | Bluestein et al. | 428/413 |
| 4,849,529 A | 7/1989 | Mizutani et al. | 549/334 |
| 4,870,193 A | 9/1989 | Taguchi et al. | 549/334 |
| 4,891,436 A | 1/1990 | Cohen et al. | 549/335 |
| 4,990,631 A | 2/1991 | Alster | 549/476 |
| 6,054,477 A | 4/2000 | Harris | 514/453 |
| 6,063,809 A | 5/2000 | Harris | 514/453 |
| 6,124,477 A | 9/2000 | Harris | 549/264 |
| 6,162,479 A | 12/2000 | Harris | 426/330.5 |
| 6,248,776 B1 | 6/2001 | Harris | 514/453 |

FOREIGN PATENT DOCUMENTS

| | | |
|---|---|---|
| DE | 1601 93 | 5/1983 |
| DE | 204 933 | 12/1983 |
| DE | 208 623 | 4/1984 |
| DE | 208 468 | 5/1984 |
| WO | WO 98/15544 | 4/1998 |
| WO | WO 98/17667 | 4/1998 |
| WO | WO 01/12616 A1 | 2/2001 |

OTHER PUBLICATIONS

Russell M.Luck et al.; "Shrinkage In Conventional Monomers During Polymerization"; Expanding Monomers: Synthesis, Characterization, and Applications; 1992 by CRC Press, Inc.; pp. 1–19; 22–51; 360–377 and 381–385.

J. Heller; "Poly (Ortho Esters)"; Advances in Polymer Sciences, 1992, vol. 107; pp. 41–92.

David G. Bourke et al.; "Conversion of 7–Methoxy–3, 4–dihydro–2H–1–benzopyran–2–one into the Corresponding Dimethyl Ortho Ester"; Tetrahedron, vol. 53, No. 11, pp. 3863–3878; 1997.

Philip Ashworth et al.; "A Method for the Chromatographic Resolution of Tetrahydropyran–2–ones"; Tetrahedron, vol. 47, No. 47, pp. 9939–9946, 1991.

Pierre Deslongchamps et al.; "The products of hydrolysis of cyclic orthoesters as a function of pH and the theory of stereoelectronic control 1.2"; Can. J. Chem, vol. 63, 1985; pp. 2485–2492.

R.A. McClelland et al.; "The hydrolysis of coumarin diethyl acetal and the lactonization of cormarinic acid ethyl ester. The partitioning of tetrahedral intermediates generated from independent sources"; Can. J. Chem, vol. 57, Feb. 19, 1979; pp. 2260–2267.

Paige R. Brooks et al.; "Boron Trichloride/Tetra–n–Butylammonium Iodide: A Mild, Selective Combination Reagent for the Cleavage of Primary Alkyl Aryl Ethers"; J. Org. Chem, vol. 64, No. 26, 1999; pp. 9719–9721.

J. D. Fourneron et al.; "Microbial Transformations. 12. Regiospecific and Asymmetric Oxidation of the Remote Double Bond of Geraniol"; J. Org. Chem., vol. 54, 1989; pp. 4686–4689.

Robert H. DeWolfe et al.; "Carboxylic Ortho Acid Derivatives Preparation and Synthetic Applications"; Academic Press; 1970; pp. 1–55 and 122–133.

Frank H. Bellevue III et al.; "Synthesis and Biological Evaluation of 6',7'-Dihydrosybergamottin (6,7–DHB), A Naturally Occurring Inhibitor of Cytochrome P450 3A4"; Biorganic & Medicinal Chemistry Letters, vol. 7, No. 20, 1997; pp. 2593–2598.

Zhi–Xian Wang et al.; "A pH Study of the Chiral Ketone Catalyzed Asymmetric Epoxidation of Hydroxyalkens"; J. Org. Chem, vol. 63, 1998; pp. 3099–3104.

M. Kamber et al.; "Synthese, H–NMR– und CD–Studien von (S)–1,2–Epoxy–1,2–dihydrolycopin und (S)–1',2'–Epoxy–1',2'–dihydro–y–carotin"; Helvetica Chimica Acta, vol. 67, 1984; pp. 968–985.

E.J. Corey et al.; "A Short and Convergent Enantioselective Synthesis of (3S)–2,3–Oxidosqualene"; Tetrahedron Letters, vol. 34, No. 38, 1993; pp. 5995–5998.

(List continued on next page.)

*Primary Examiner*—Amelia A. Owens
(74) *Attorney, Agent, or Firm*—Oblon, Spivak, McClelland, Maier & Neustadt, P.C.

(57) ABSTRACT

Ortho esters and ortho carbonates can be produced by alkylating esters and carbonates with, for example, the hexafluorophosphate salt of a trialkyl oxonium ion. The spiro species are useful intermediates in the synthesis of complex organic molecules. Synthetic pathways for the production of medically active compounds incorporates spiro ortho esters. Anti-first-pass effect materials are produced in high yield utilizing a synthetic strategy incorporating cyclic ortho ester intermediates.

19 Claims, 3 Drawing Sheets

OTHER PUBLICATIONS

Mitsuaki Kodama et al.; "Convenient Synthesis of Chiral Epoxyisoprenoids By Yeast Reduction"; Tetrahedron Letters, vol. 31, No. 28, 1990; pp. 4025–4026.

W. Eschenmoser et al.; "Synthesen der enantiomeren Aleuriaxanthine. Nachweis eines vorherrschenden (Z)–Aleurixanthins in Aleuria"; Helvetica Chimica Acta, vol. 66, Fasc. 1, 1983; pp. 82–91.

X.M. Zhang et al.; "Asymmetric Dihydroxylation of the Remote Double Bond of Geraniol; A Unique Stereochemical Control Allowing Easy Access to Both Enantiomers of Geraniol–6,7–diol"; J. Org. Chem., vol. 56, 1991; pp. 3814–3817.

M. Stankovicova et al.; "Kinetics of Alkaline Hydrolysis and Other Physico–chemical Properties of the Basic Ethyl Esters of Phenylcarbamic Acid"; Turkey Pharmazie, vol. 52, No. 11, 1997; pp. 881–882, 814.

J. Berner; "Zur Kinetik der Saurekatalysierten Hydrolyse von Carbamidsaureestern"; Z. Chem., vol. 22, 1982; pp. 221–222.

Heidi Meier et al.; "12. Optisch aktive Lycopin–epoxide und Lycopin–glycole: Synthesen und chiroptische Eigenschaften"; Helvetica Chimica Acta, vol. 69, 1986; pp. 106–123.

Kenji Mori et al.; "Synthesis of Both The Enantiomers of Juvenile Hormone III+"; Tetrahedron, vol. 43, No. 18, 1987; pp. 4097–4106.

Rudolf Schwabe et al.; "32.Synthese von (–)–(R)–Nephthenol und (–)–(R)–Cembren A"; Helvetica Chimica Acta, vol. 71, 1988; pp. 292–297.

Barry M. Trost et al.; "Sulfur–Substituted Dienes and the Silylene Protecting Group in Synthesis Deoxypillaromycinone"; J. Org. Chem, vol. 48, 1983; pp. 3252–3265.

L. Haase et al.; "Untersuchungen an Spiroorthoester–Copolymeren"; Acta Polymerica, vol. 40, 1989; pp. 229–233.

E. Klemm et al.; "Untersuchungen zur Substanzpolymerisation spirocyclischer Orthoester mit $Et_3O+SbCl_6$"; Acta Polymerica, vol. 33, 1982; ; pp. 429–432.

George A. Olah et al.; "Preparative Carbocation Chemistry; VI Advantageous Stable and Soluble Fluorophosphate Salts; Trialkyloxonium, Trialkylcarboxonium, and Dialkoxycarbenium Hexafluorophosphates"; Synthesis, Aug. 1973; pp. 490–492.

Pierre Deslongchamps et al.; "The Hydrolysis of Cyclic Orthoesters, Stereoelectronic Control in the Cleavage of Hemiorthoester Tetrahedral Intermediates"; Can. J. Chem., vol. 53, 1975; pp. 1601–1615.

Alza Technologies website; "Alzamer Depot Technology"; downloaded Jul. 16, 2001; 5 pages.

Letter dated Jul. 10, 2001, from Bioavailability Systems, LLC to Chemical Abstracts Service, Client Services; 1 page. Chemical Abstracts Service, Client Services Order No. 61840.

S. O. De Silva et al.; "A convergent route to phthalideisoquinoline alkaloids via directed metalation of tertiary benzamides"; Can. J. Chem.; vol. 57, 1979; pp. 1598–1605.

Advanced Polymer Systems; "Bioerodible Technology"; 2001; 2 pages.

Advanced Polymer website; "Safety Eval of Biochronomer"; downloaded Jul. 16, 2001; 2 pages.

P = protecting group

P = protecting group

SYNTHESIS OF SPIRO ESTERS, SPIRO ORTHO CARBONATES, AND INTERMEDIATES

This application is a Continuation Application of U.S. application Ser. No. 09/982,827, filed Oct. 22, 2001 now U.S. Pat. No. 6,613,918, now allowed, which is a Non-Provisional of Provisional Application Serial No. 60/241,850, filed Oct. 20, 2000.

BACKGROUND OF THE INVENTION

1. Field of the Invention

The present invention relates to the synthesis of cyclic and spiro ortho esters and cyclic and spiro ortho carbonates, and to the synthesis and use of intermediates useful in the synthesis and production of cyclic and spiro ortho esters as well as cyclic and spiro ortho carbonates. The synthesis of anti-first-pass effect compounds containing spiro ortho ester groups is also included in the invention.

2. Discussion of the Background

Compositions exhibiting anti-first-pass effect activity are known to contain spiro ortho ester groups. Specifically, it has recently been shown that the compounds in citrus extracts responsible for the anti-first-pass effect contain spiro ortho esters (see e.g., U.S. Pat. Nos. 6,063,809 and 6,054,477, both incorporated herein by reference). In pharmaceutical applications, polymers synthesized from ortho esters have shown usefulness in drug delivery devices (see e.g. U.S. Pat. No. 4,990,631, incorporated herein by reference).

Molecules containing cyclic and spiro ortho ester and ortho carbonate groups have been shown to exhibit properties and chemical behavior of potential economic value. For example, monomers containing spiro ortho ester and spiro ortho carbonate groups, when incorporated into polymer systems, can reduce or eliminate the shrinkage that is commonly associated with thermosetting or thermoplastic polymerization processes. In fact, polymerization of monomers containing spiro ortho ester and spiro ortho carbonate groups can afford a product whose volume is nearly 10% greater than the volume of the monomer starting material (R. K. Sadhir and R. M. Luck, *Expanding Monomers: Synthesis, Characterization and Applications*, CRC Press, Inc., 1992). Advantages of monomers that expand (or do not shrink) upon polymerization include the ability to effect complete mold filling and mold replication (i.e., to produce precision-cast parts), the production of strain-free parts, and the increase in bonding strength of adhesive glues, coatings, etc.

While molecules and materials containing or synthesized from spiro ortho esters and spiro ortho carbonates have shown significant promise in both the medical and polymer industries, their commercial use remains limited. The lack of availability of sufficient quantities of spiro ortho ester and spiro ortho carbonate materials is one factor inhibiting the economic exploitation and further development of these materials. Although synthetic routes to spiro ortho esters and spiro ortho carbonates are known and have been described in the literature, they have thus far not lent themselves to inexpensive, large-scale production. For example, a reference book on the subject estimates that the high cost of the monomers (approximately $1000 per pound for spiro ortho carbonates) has severely limited the competitiveness of the technology (R. K. Sadhir and R. M. Luck, *Expanding Monomers: Synthesis, Characterization, and Applications*, CRC Press, Inc., 1992, page 385). As a further example, U.S. Pat. No. 4,387,215 addresses the cost and availability issue by suggesting that spiro ortho ester and spiro ortho carbonate monomers can be diluted with cheaper materials that do not expand upon polymerization. A synthetic method operable on a large scale would offer formulators, researchers, and developers greater opportunity to take advantage of the unique physical and chemical properties of spiro ortho esters and spiro ortho carbonates.

The improved syntheses of cyclic ortho esters and cyclic ortho carbonates, as described herein, are useful because these chemicals serve as intermediates for the valuable spiro ortho ester and spiro ortho carbonate materials discussed above. Cyclic ortho esters and cyclic ortho carbonates have direct, additional value, however, because they have proven useful in making drug delivery devices. For example, polymers produced from cyclic ortho esters have demonstrated sustained systemic delivery of proteins and other expensive agents for periods ranging from days to weeks (see, for example, Alza Technologies website, "Alzamer Depot Technology"; *Advances in Polymer Science*, 107, pp. 41–92, (1992)).

DESCRIPTION OF THE RELATED ART

The polymerization of spiro ortho esters in the presence of oxonium ions stabilized with, for example, antimonate salts can yield polymeric materials having low volume shrinkage and special optical properties. The oxonium salt is used to initiate polymerization via ring opening metathesis polymerization (ROMP), see U.S. Pat. No. 4,387,215. Similar salts have been used in the bulk polymerization of spiro ortho esters. The use of either an oxonium or carbonium salt is a common feature in the polymerization or ring opening of cyclic and spiro ortho esters.

The difficulty in purifying and isolating spiro ortho ester monomers led practitioners to initiate and complete polymerization on unpurified spiro ortho ester starting materials (U.S. Pat. No. 4,738,899). Poly ortho esters can be formed in a "one-pot" reaction by heating intermediate ortho esters. Combining a vicinal diol with a compound of formula R'C(OEt)$_3$ was shown to first form an intermediate cyclic ortho ester. Heating the reaction mixture to 100° C. in a high boiling solvent allowed removal of the EtOH formed as a by-product of the trans orthoesterification reaction which subsequently allowed an increased rate of reaction to be realized (Advances in Polymer Science, 107, pp. 41–92, (1992).

The use of "Meerwein's reagent" to form ortho esters or ortho carbonates is known in the art (see for example, Tetrahedron, 53(11), 3863 (1997); Tetrahedron, 47(47), 9939 (1991); Can. J. Chem., 63, 2485 (1985); Can. J. Chem., 57, 1601 (1979); Can. J. Chem., 57, 2260 (1979)). Meerwein's reagent is an alkylating agent of formula [R$_3$O][X] where the R group can be Me, Et, etc. and the counterion X is usually BF$_4$. The reaction conditions call for reacting a stoichiometric or an excess amount of the alkylating agent with a lactone or cyclic carbonate followed by the addition of a large excess of a nucleophile at low temperature. This reaction strategy can give low yields and complicated reaction product mixtures depending on the functionalization of the lactone or the cyclic carbonate.

U.S. Pat. No. 4,990,631 describes a process for preparing cyclic ortho esters from lactones using tetrafluoroborate salts generated from triethyl formate and boron trifluoride. Spiro ortho carbonates containing an ipso carbon sigma bonded to four oxygen atoms have been prepared in the presence of nucleophiles (U.S. Pat. Nos. 4,891,436; 4,870,193 and 4,849,529).

In view of the state of the art, a reliable synthetic method for cyclic and spiro ortho esters and ortho carbonates has so far not been forwarded. What is more, the complex mixture of materials obtained by extracting a citrus product makes it expensive to isolate a pure anti-first-pass effect product of reliable and consistent quality. In this regard a reliable and reproducible synthetic method for constructing spiro and cyclic ortho esters and carbonates will aid in the synthesis of these materials that in turn will allow their commercial exploitation in medical applications, polymer technology, etc.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings.

SUMMARY OF THE INVENTION

Objects of the Present Invention

Figure 1:
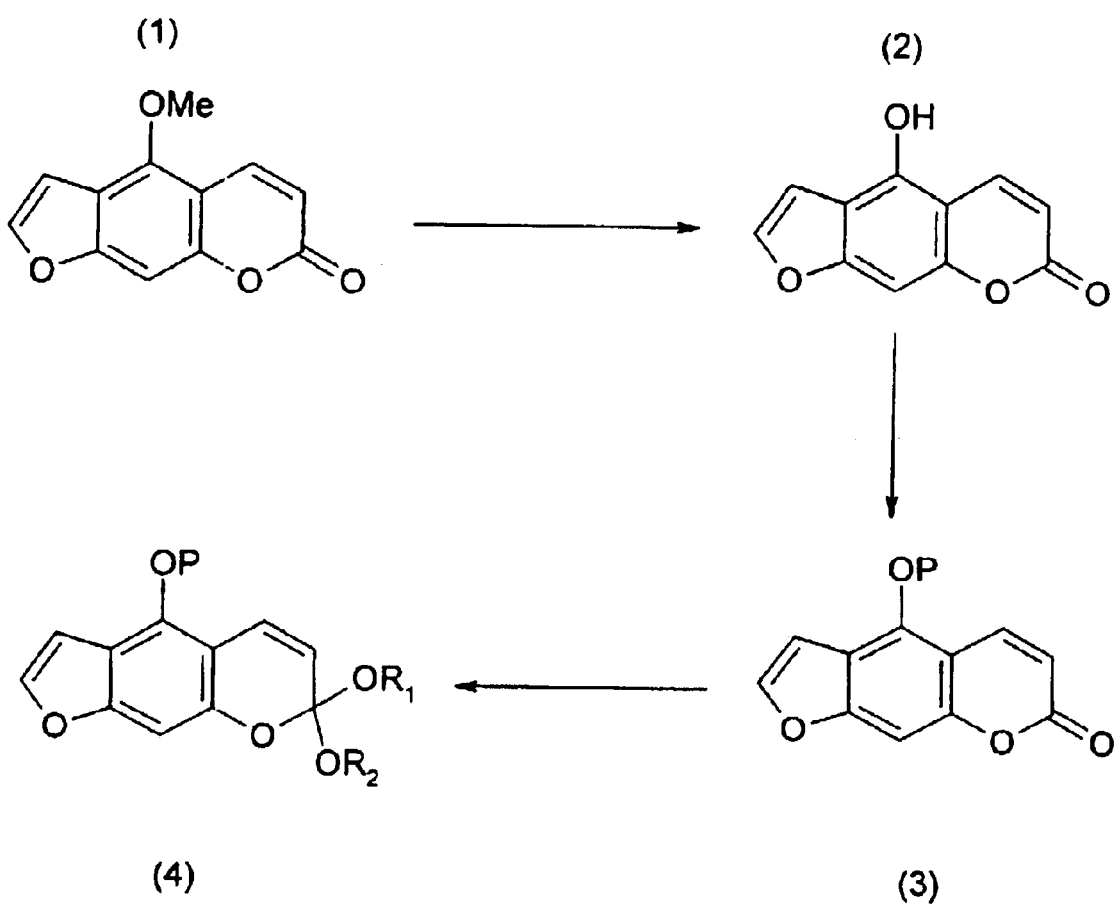
FIG. 1 depicts the steps of the conversion of Bergapten to a protected cyclic ortho ester intermediate that is useful in the synthesis and production of an anti-first-pass effect compound.

One object of the present invention is to provide a method for synthesizing cyclic ortho esters, spiro ortho esters, cyclic ortho carbonates, and spiro ortho carbonates that preferably can be operated on a commercial scale.

It is another object of the present invention to provide a method for synthesizing anti-first-pass compounds containing a spiro ortho ester functionality.

Scheme I shown below depicts the steps of the generalized conversion of a lactone to an ortho ester and Scheme III shows the conversion of a carbonate to an ortho carbonate. The synthesis of acyclic, cyclic and spiro ortho esters can be carried out by first reacting an ester with an agent, sometimes termed an alkylating agent, then treating the reaction mixture with an excess of alkoxide to produce an ortho ester (I). The ortho ester thus obtained may be reacted with a vicinal diol to yield the cyclic or spiro ortho ester (II) (in this application the term "spiro" denotes two ring structures sharing only one carbon in common; thus, in I if R' and $R_2$ are connected it is a cyclic ortho ester; in (II) if $R^1$ and $R^2$ are connected it is a spiro ortho ester, if in (II) they are not connected it is a cyclic ortho ester). Similarly, acyclic, cyclic and spiro ortho carbonates can be produced by reaction of a carbonate with an alkylating agent then treating the reaction mixture with an alkoxide to produce an ortho carbonate (III). The ortho carbonate may be reacted with a vicinal diol to produce the corresponding cyclic or spiro ortho carbonate (IV).

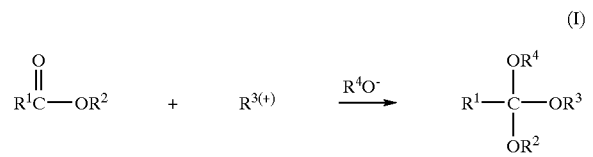

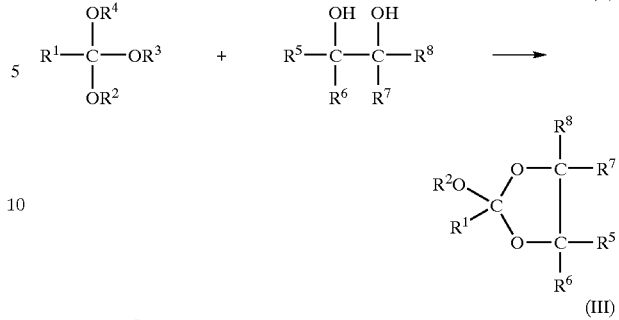

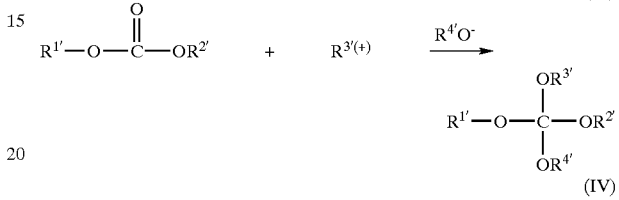

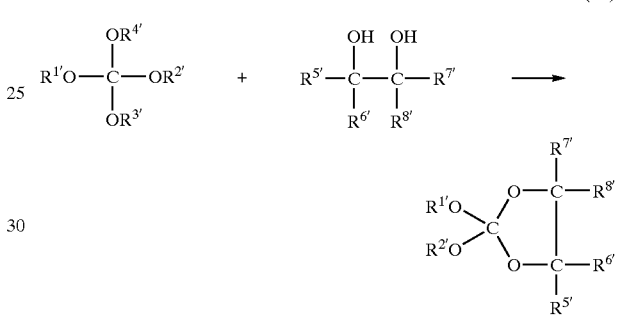

As noted above, the starting esters and carbonates may be cyclic species (wherein R1 and R2 or R1' and R2' are connected) in which case cyclic ortho esters and spiro ortho esters (also known as spirocyclic ortho esters) and cyclic ortho carbonates and spiro ortho carbonates (also known as spirocyclic ortho carbonates) are produced. The substituents R1, R2, R3, R4, R5, R6, R7, R8, R1', R2', R3', R4', R5', R6', R7', and R8' may individually be any organic or oganometallic group, including, but not limited to, linear, branched or cyclic alkanes, polycyclic groups, aromatic groups, mixed aromatic-aliphatic polycyclic groups, metal-organic groups, etc. The R substituents noted here may have 1–40, preferably 1–20, carbons and may be any and all organic or organometallic species constituted of the atoms C, O, N, P, S, H, etc. In this sense, the terms "alkylating agent" and "alkoxide" as used herein do not limit the $R^3$ and $R^{3'}$ or $R^4$ and $R^{4'}$ species to alkyl groups but instead are used to denote the chemical function of these species in regard to its addition to the starting ester or carbonate, etc. The R substituent described here may, of course, be unsubstituted or substituted with any and all functionalities. Examples of such functionalities include OR where R is any alkyl or aromatic group, $C_{1-20}$ preferred, $NR_3$ where R is defined as R, R1, etc., above, etc. In this sense the invention methods reside in the causation at the various reaction centers, and not in the identity of the particular appended substituents. Those of ordinary skill in the art are well suited to carry out the invention reactions as described herein with broad variation in regard to the organic groups surrounding the reaction center in view of the guidance provided herein. In addition, those of ordinary skill in the art are familiar with the use of protecting groups, etc. Thus, it is not the organic and/or organometallic groups "R" as described above that are of particular importance herein where the invention is described in generic terms, but rather the causation of the reaction at the reaction center. This is true for all generic invention reactions described herein, and applies to cyclic ortho esters, spiro ortho esters, spiro ortho carbonates and cyclic ortho carbonates with equal force.

As noted, the present invention provides a method for synthesizing cyclic and spiro ortho esters. According to the invention, a method is provided for synthesizing compounds like (4) in FIG. 1. See also Scheme 1 above. Ortho esters of this type are preferred intermediates in the synthesis of compounds that exhibit the anti-first-pass effect.

The synthesis of cyclic ortho esters like those of formula (4) begins with the conversion of the OMe ether linkage in Bergapten (1) to a hydroxyl (2). The phenolic hydroxyl of formula (2) is treated with a protecting group to avoid undesired reaction of the acidic phenolic proton with other reagents later in the synthetic procedure. Protection of the hydroxyl group forms (3) which is converted to the cyclic ortho ester by alkylation followed by treatment with a nucleophile.

The present method also provides for the total synthesis of the anti-first-pass effect compounds disclosed in U.S. Pat. Nos. 6,054,477; 6,063,809; 6,124,477; 6,162,479 and 6,248,776, incorporated herein by reference, including all formulae presented therein and including compound (10) in FIG. 3, utilizing the cyclic ortho ester synthesis above. Compounds that can be made by the invention process include compounds A through N and I–XVI shown below where $Z_1$ through $Z_{12}$ are R or L-E, as defined below. Descriptive and tabular definitions of substituents $Z_1$ through $Z_{12}$ are presented in U.S. Pat. No. 6,248,776 (62 pages), and they are incorporated herein by reference in the interest of brevity. The following includes some of this information.

In each of the structures below, R is, independently, H or an optionally substituted $C_1$–$C_{15}$ alkyl group, L is an optionally substituted $C_1$–$C_{15}$ linear or branched, saturated, monounsaturated or polyunsaturated alkyl group optionally interrupted by one or plural nonadjacent sulfur or oxygen atoms and optionally terminated at one or both ends by oxygen, HAr is an optionally substituted $C_6$–$C_{24}$ aromatic group or heteroaromatic group optionally containing one or plural ring atoms selected from the group consisting of N, O, S, and P, and E is —H, —OH, —COOH, —COOR (where R is defined above) or an optionally substituted $C_1$–$C_8$ linear or branched, saturated, monounsaturated or polyunsaturated alkyl group optionally interrupted by one or plural nonadjacent oxygen or sulfur atoms, or E is a $C_3$–$C_8$ optionally substituted cyclic saturated, monounsaturated or polyunsaturated alkyl group optionally interrupted by one or plural nonadjacent oxygen or sulfur atoms, or E is optionally substituted HAr. Preferably, the compounds do not contain a peroxide (O—O) group. Disulfide groups (S—S) are not preferred, but may be present. Preferably E is an epoxide or dihydroxy radical such as —CH(OH)$_2$. E may also be an acid-opened epoxide group.

The compounds of the invention as described above are unlimited with regard to stereochemistry, E-Z isomerism and all possibilities are included. Racemic mixtures are included as are each and every enantiomer and diastereomer.

The groups R, L, HAr, and E may optionally be substituted with a $C_1$–$C_6$ linear, branched or cyclic alkyl group, —OH, a halogen atom, a $C_1$–$C_5$ alkoxy group, a $C_1$–$C_5$ alkylcarbonyloxy group, a $C_1$–$C_5$ alkoxycarbonyl group, etc. Such substituents also may be optionally substituted directly on the ring structures regardless of whether such substituents appear on R, L, HAr or E.

In the invention compounds a preferred group of substituents, optional and otherwise, comprise the following: hydrogen, $C_1$–$C_4$ alkyl, —S($C_1$–$C_4$ alkyl), —O($C_1$–$C_4$ alkyl), —NH$_2$, —NH($C_1$–$C_4$ alkyl), —N($C_1$–$C_2$ alkyl)($C_1$–$C_4$ alkyl), hydroxy, —O($C_1$–$C_2$ alkyl), fluoro, $C_1$–$C_6$ alkyl, chloro, bromo, iodo, $C_1$–$C_4$ alkoxy, —CF$_3$, —C(=O)O—($C_1$–$C_4$) alkyl, —OC(=O)($C_1$–$C_4$ alkyl), —OC(=O)N($C_1$–$C_4$ alkyl)($C_1$–$C_2$ alkyl), —NHCO($C_1$–$C_4$ alkyl), —COOH, —COO($C_1$–$C_4$ alkyl), —CONH($C_1$–$C_4$ alkyl), —CON($C_1$–$C_4$ alkyl)($C_1$–$C_2$ alkyl), —S($C_1$–$C_4$ alkyl), —CN, —NO$_2$, —SO($C_1$–$C_4$ alkyl), —SO$_2$($C_1$–$C_4$ alkyl), —SO$_2$NH($C_1$–$C_4$ alkyl) and —SO$_2$N($C_1$–$C_4$ alkyl)($C_1$–$C_2$ alkyl).

Another group of preferred substituents, optional and otherwise, comprise: $C_1$–$C_{12}$ alkyl, aryl, ($C_1$–$C_4$ alkylene) aryl, phenyl, naphthyl, thienyl, benzothienyl, pyridyl, quinolyl, pyrazinyl, pyrimidinyl, imidazolyl, furanyl, benzofuranyl, benzothiazolyl, isothiazolyl, pyrazolyl, pyrrolyl, indolyl, pyrrolopyridyl, oxazolyl and benzoxazolyl, $C_3$$C_8$ cycloalkyl or ($C_1$–$C_6$ alkylene)($C_3$–$C_8$ cycloalkyl), $C_1$–$C_4$ alkyl, benzyl, $C_1$–$C_4$ alkanoyl, $C_1$–$C_6$ alkoxy, —OC(=O)($C_1$–$C_6$ alkyl), —OC(=O)N($C_1$–$C_4$ alkyl)($C_1$–$C_2$ alkyl), —S($C_1$–$C_6$ alkyl), amino, —NH ($C_1$–$C_2$ alkyl), —N($C_1$–$C_2$ alkyl)($C_1$–$C_4$ alkyl), —N($C_1$–$C_4$ alkyl)-CO-($C_1$–$C_4$ alkyl), —NHCO($C_1$–$C_4$ alkyl), —COOH, —COO($C_1$–$C_4$ alkyl), —CONH($C_1$–$C_4$ alkyl), —CON($C_1$–$C_4$ alkyl) ($C_1$–$C_2$ alkyl), —SH, —SO($C_1$–$C_4$ alkyl), —SO$_2$($C_1$–$C_4$ alkyl), —SO$_2$NH($C_1$–$C_4$ alkyl) and —SO$_2$N($C_1$–$C_4$ alkyl)($C_1$–$C_2$ alkyl).

Another group of preferred substituents, optional and otherwise, comprise: $C_1$–$C_{12}$ alkyl, aryl, ($C_1$–$C_4$ alkylene) aryl, phenyl, naphthyl, thienyl, benzothienyl, pyridyl, quinolyl, pyrazinyl, pyrimidinyl, imidasolyl, furanyl, benzofuranyl, benzothiazolyl, isothiazolyl, pyrazolyl, pyrrolyl, indolyl, pyrrolopyridyl, oxazolyl and benzoxazolyl, $C_3$$C_8$ cycloalkyl or ($C_1$–$C_6$ alkylene)($C_3$–$C_8$ cycloalkyl), $C_1$–$C_4$ alkyl, benzyl, $C_1$–$C_4$ alkanoyl, $C_1$–$C_6$ alkoxy, —OC(=O)($C_1$–$C_6$ alkyl), —OC(=O)N($C_1$–$C_4$ alkyl)($C_1$–$C_2$ alkyl), —S($C_1$–$C_6$ alkyl), amino, —NH ($C_1$–$C_2$ alkyl), —N($C_1$–$C_2$ alkyl)($C_1$–$C_4$ alkyl), —N($C_1$–$C_4$ alkyl)-CO-($C_1$–$C_4$ alkyl), —NHCO($C_1$–$C_4$ alkyl), —COOH, —COO($C_1$–$C_4$ alkyl), —CONH($C_1$–$C_4$ alkyl), —CON($C_1$–$C_4$ alkyl) ($C_1$–$C_2$ alkyl), —SH, —SO($C_1$–$C_4$ alkyl), —SO$_2$($C_1$–$C_4$ alkyl), —SO$_2$NH($C_1$–$C_4$ alkyl) and —SO$_2$N($C_1$–$C_4$ alkyl)($C_1$–$C_2$ alkyl).

A third group of preferred substituents, optional and otherwise, comprise: —S($C_1$–$C_4$ alkyl) or —SO$_2$($C_1$–$C_4$ alkyl)($C_1$–$C_6$ alkyl), —N($C_1$–$C_4$ alkyl)($C_1$–$C_2$ alkyl), —S($C_1$–$C_4$ alkyl), —SO($C_1$–$C_4$ alkyl), —CO($C_1$–$C_4$ alkyl), —C(=O)H, —C(=O)O($C_1$–$C_4$ alkyl), $C_1$–$C_3$ alkoxy, dimethylamino, methylamino, ethylamino, —NHC(=O)CH$_3$, $C_1$–$C_3$ thioalkyl, —COOH, —C(=O)O($C_1$–$C_4$ alkyl), —NO$_2$, phenyl, naphthyl, thienyl, benzothienyl, pyridyl, quinolyl, pyrazinyl, furanyl, benzofuranyl, benzothiazolyl, benzisothiazolyl, benzisoxazolyl, benzimidazolyl, indolyl, benzoxazolyl or $C_3$–$C_8$ cycloalkyl, chloro, $C_1$–$C_6$ alkyl, —O($C_1$–$C_6$ alkyl) bromo, iodo, formyl, —CN, —CF$_3$, —NO$_2$, —NH$_2$, —NH($C_1$–$C_4$ alkyl), —N($C_1$–$C_2$ alkyl) ($C_1$–$C_6$ alkyl), —C(=O)O($C_1$–$C_4$ alkyl), —C(=O)($C_1$–$C_4$ alkyl), —COOH, —SO$_2$NH($C_1$–$C_4$ alkyl), —SO$_2$N($C_1$–$C_2$ alkyl)($C_1$–$C_4$ alkyl), —SO$_2$NH$_2$, —NHSO$_2$($C_1$–$C_4$ alkyl), —S($C_1$–$C_6$ alkyl) and —SO$_2$($C_1$–$C_6$ alkyl), fluoro, hydroxy, amino, methylamino, dimethylamino, acetyl, hydrogen, $C_1$–$C_4$ alkyl, halo (e.g., chloro, fluoro, iodo or bromo), hydroxy, —O($C_1$–$C_4$ alkyl), —C(=O)($C_1$–$C_4$ alkyl), —C(=O)O($C_1$–$C_4$ alkyl), —$OCF_3$, —$CF_3$, —$CH_2OH$ or —$CH_2O$($C_1$–$C_2$ alkyl) hydroxy, methoxy and fluoro.

Within these three groups of preferred substituents are also specific examples of HAr (i.e., $C_6$–$C_{24}$ aromatic groups or heteroaromatic groups).

In addition, for the compounds listed the definition of R is expanded to include, independently, hydrogen and all those groups identified above as optional substituents (e.g., $C_1$–$C_6$ linear, branched or cyclic alkyl group, —OH, a halogen atom, etc., hydrogen, $C_1$–$C_4$ alkyl, —S($C_1$–$C_4$ alkyl), etc., $C_1$–$C_{12}$ alkyl, aryl, ($C_1$–$C_4$ alkylene) aryl, etc., —S($C_1$–$C_4$ alkyl) or —SO($C_1$–$C_4$ alkyl)($C_1$–$C_6$ alkyl), etc.).

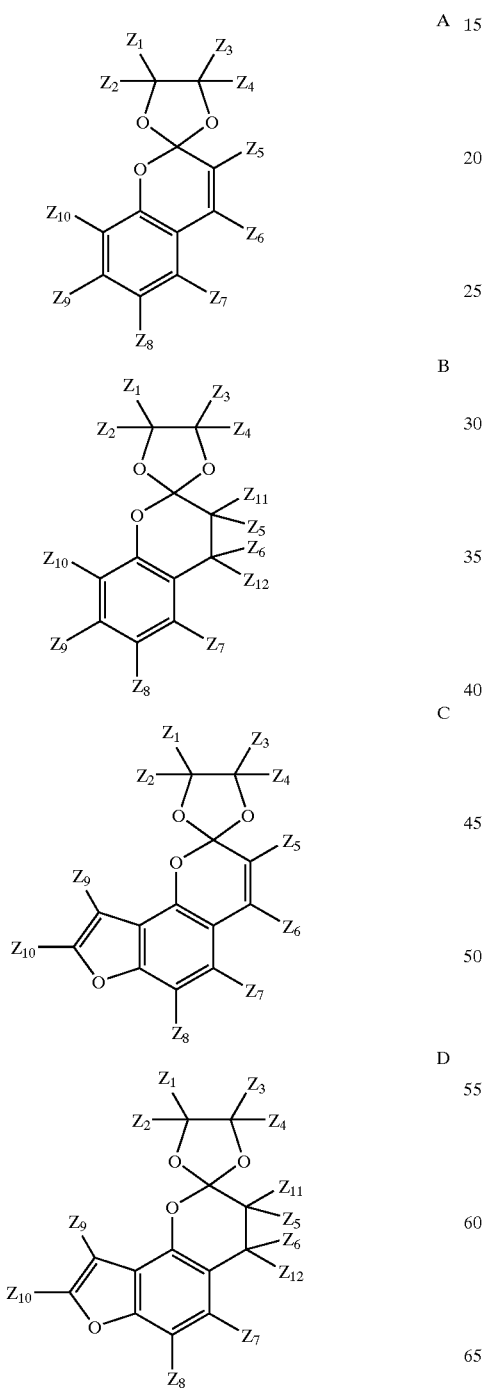

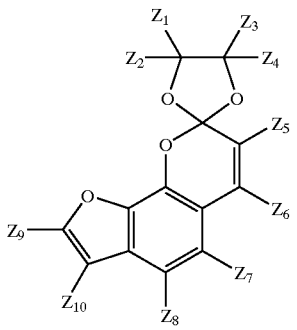

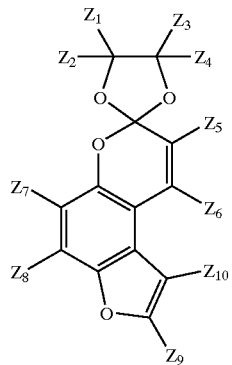

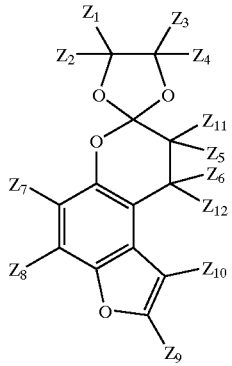

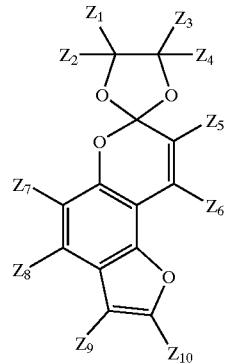

-continued

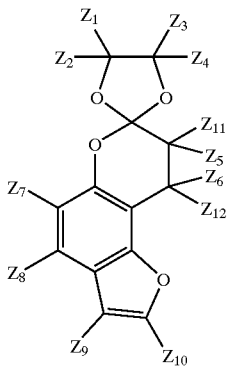

I

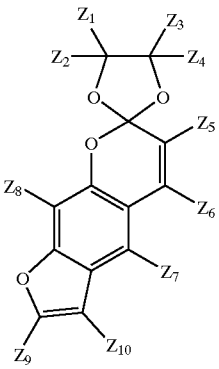

M

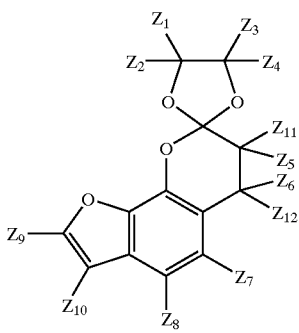

J

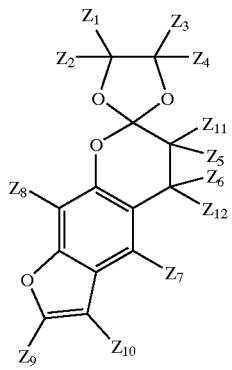

N

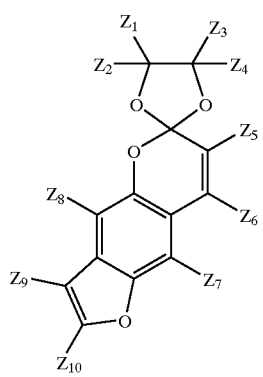

K

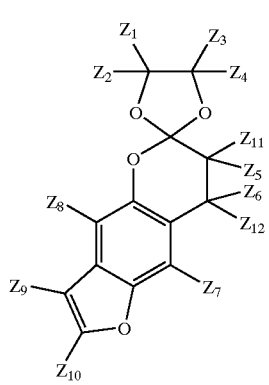

L

Figure 2:
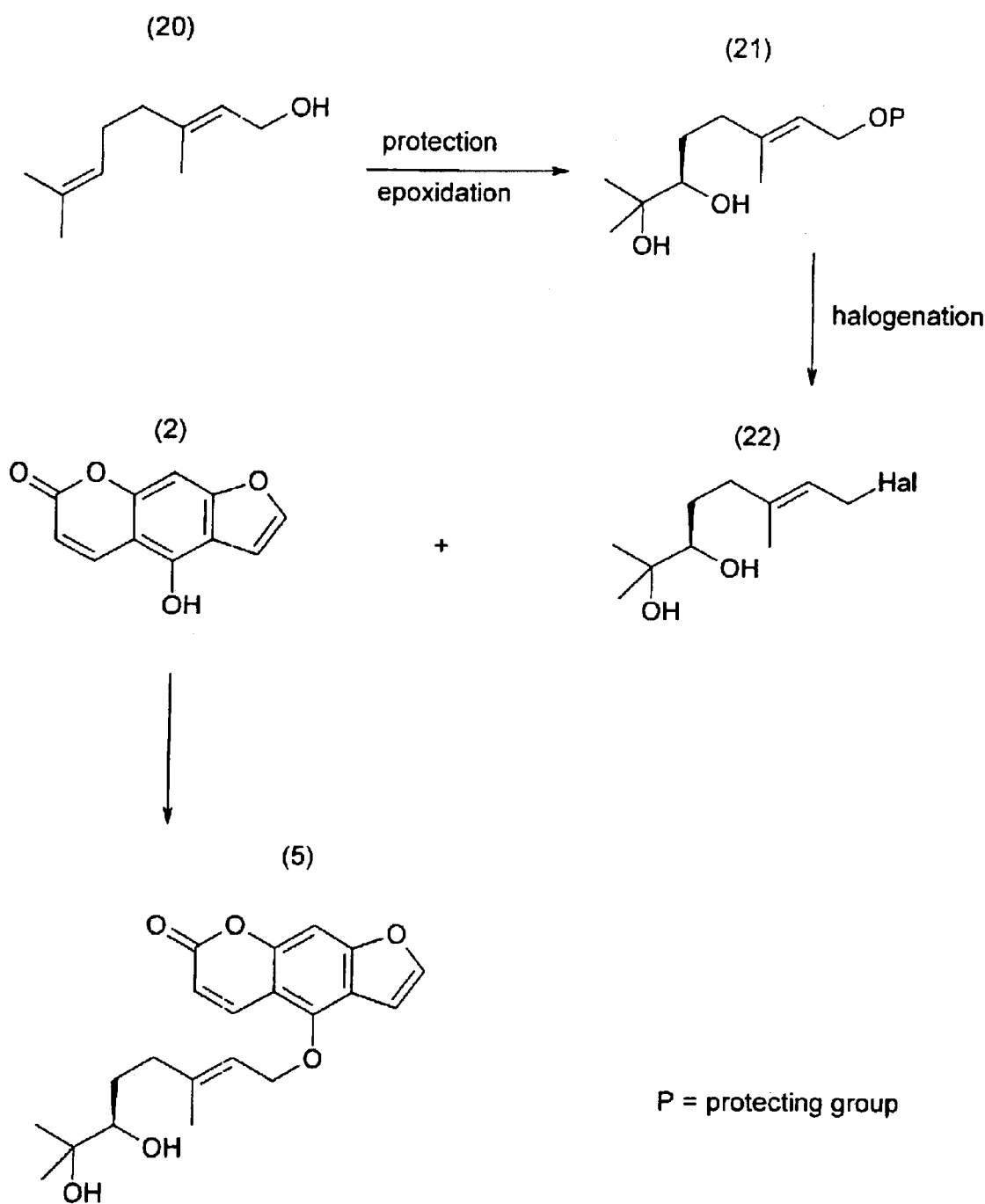
FIG. 2 provides a reaction sequence for converting geraniol to the halogenated diol used as an alkylating agent in the synthesis of an anti-first-pass effect compound and its use to alkylate Bergapten.

In this synthesis (the generic synthesis is herein explained with regard to compound (10)) a sidechain component of the anti-first-pass effect compound (10) is first derived from geraniol (20) by the synthetic route schemed in FIG. 2. Reaction of geraniol with phenylisocyanate, epoxidation, and hydrolysis forms the chiral diol (21) in for example 88% ee optical purity. The diol group of (21) can optionally be protected by reaction with 2,2-dimethoxypropane (2,2-DMP) to yield an acetonide or can be protected with other groups (e.g., various silyl groups). After removing the carbonate, the freed terminal hydroxyl is converted to a halide and deprotected to form (22) or may remain protected (see 22A in FIG. 3) for use in the synthesis of the anti-first-pass effect compound (10).

The formation of (10) includes combining the carbon skeletons of two molecules derived from Bergapten (1) and two molecules derived from geraniol (20). Both Bergapten and geraniol are readily available materials.

In the scheme shown in FIG. 2 the diol halide (22) is reacted with Bergaptol (2) in a 1:1 molar ratio, and the alkylation product (5) results.

Figure 3:
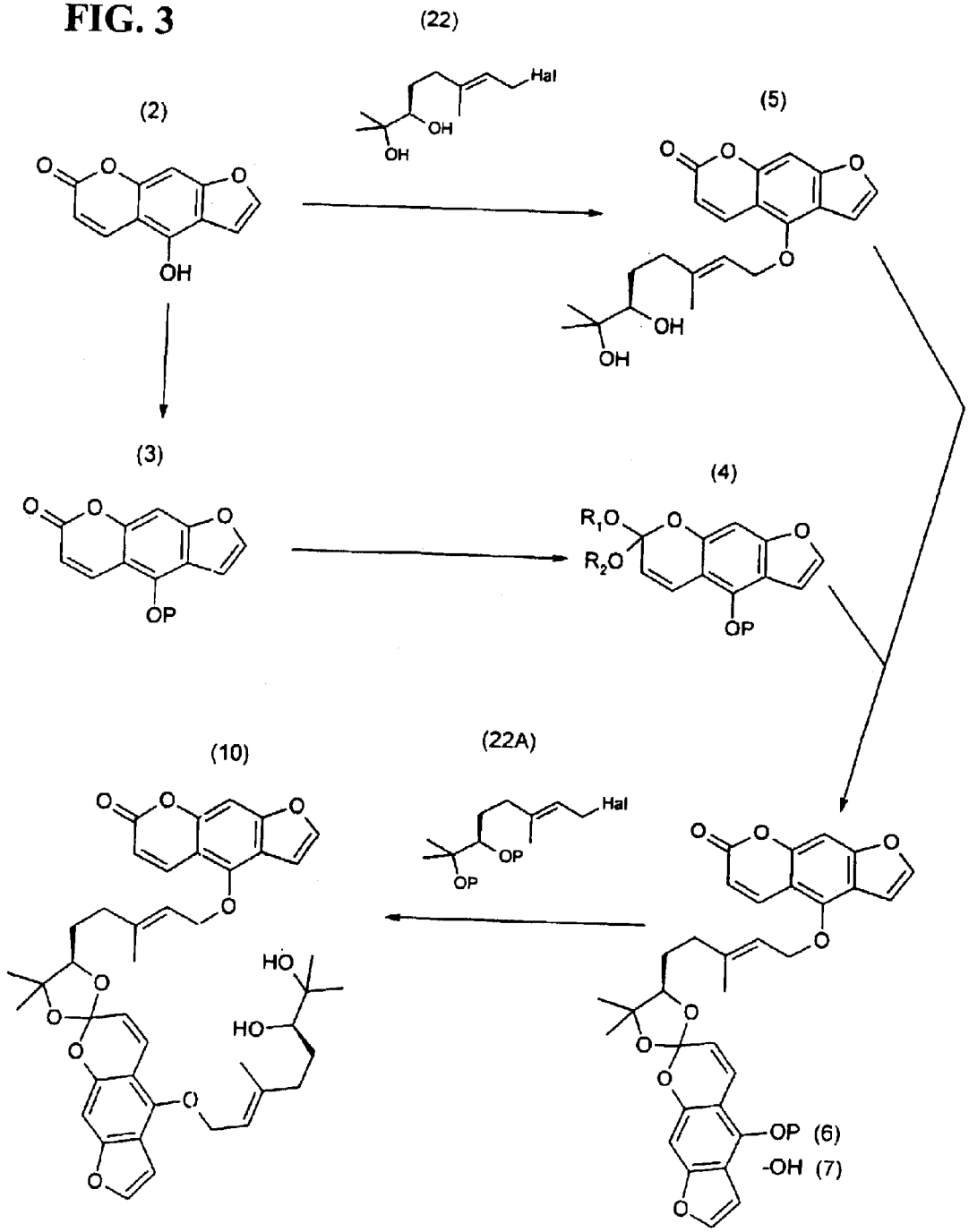
FIG. 3 shows a reaction pathway for synthesizing a spiro ortho ester that exhibits the anti-first-pass effect.

FIG. 3 shows that a precursor (6) to the anti-first-pass effect compound (10) is produced by reaction of the cyclic ortho ester (4) with the alkylated Bergaptol (5). Conversion of (6) to the free phenol (7) is followed by reaction with one equivalent of the halogenated diol (22) or its protected equivalent (22A) to yield the desired spiro ortho ester anti-first-pass effect compound (10).

Other compounds which may be synthesized by this general route include:

I
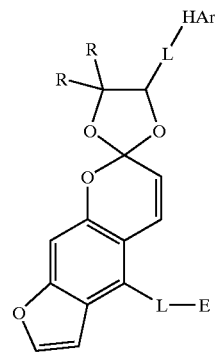
II
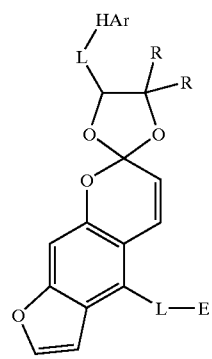
III
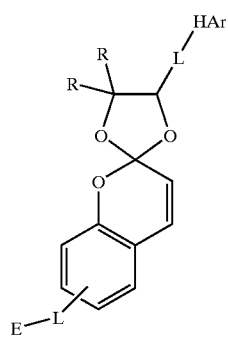
IV
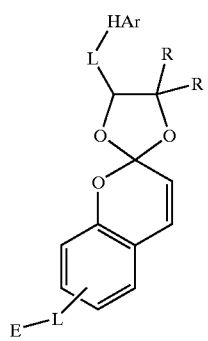
V
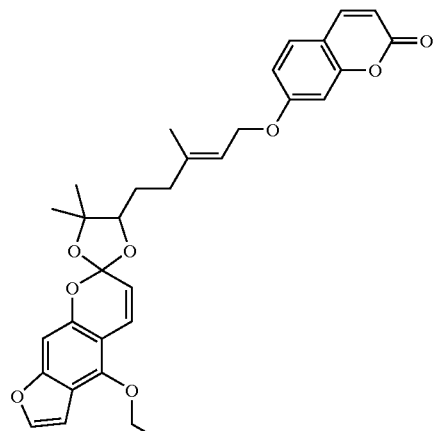
VI
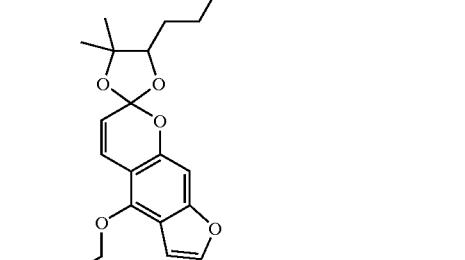
VII
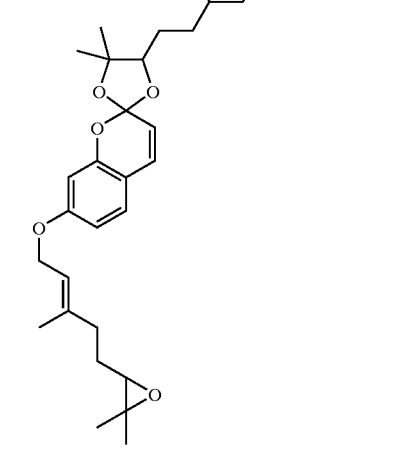

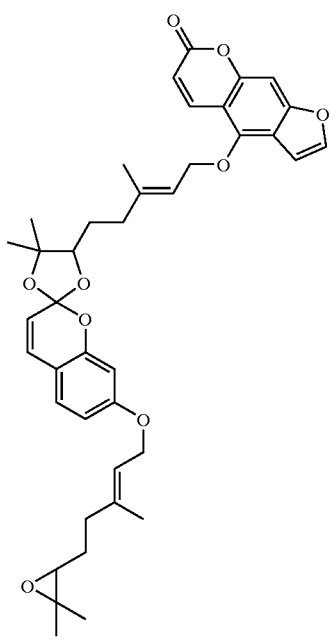
VIII
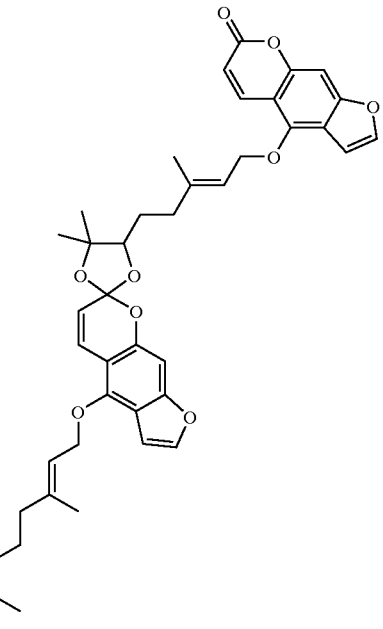
X
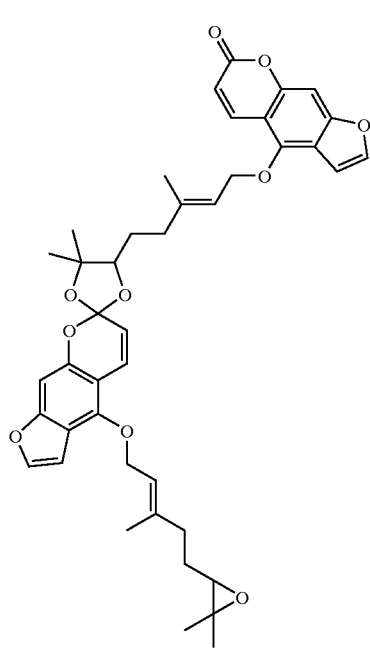
IX
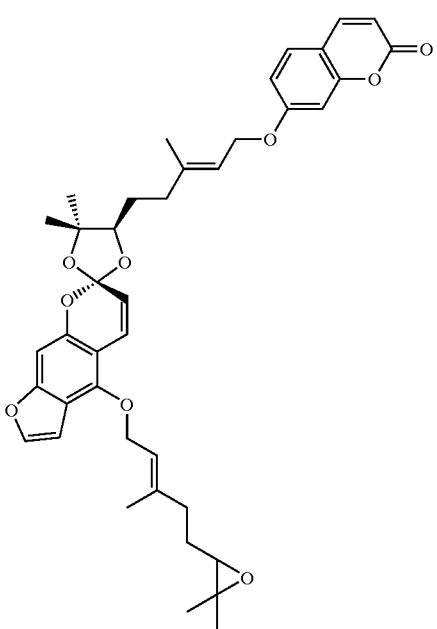
XI

XII
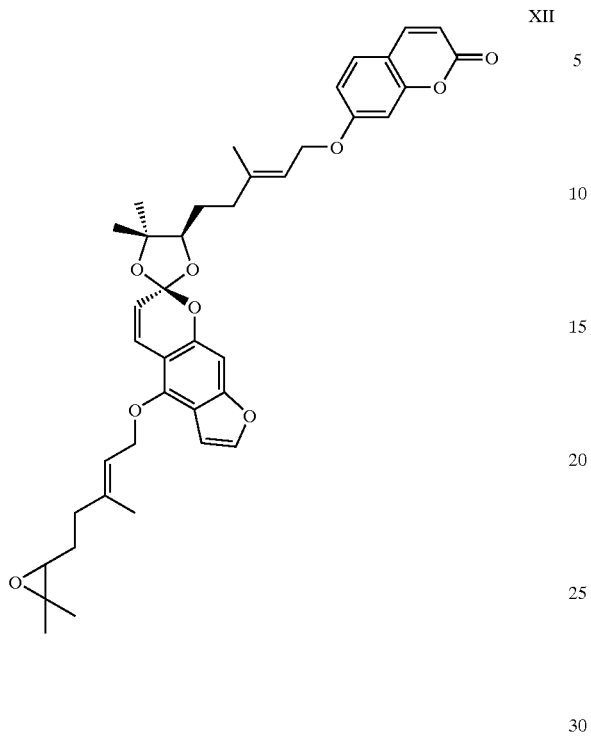
XIV
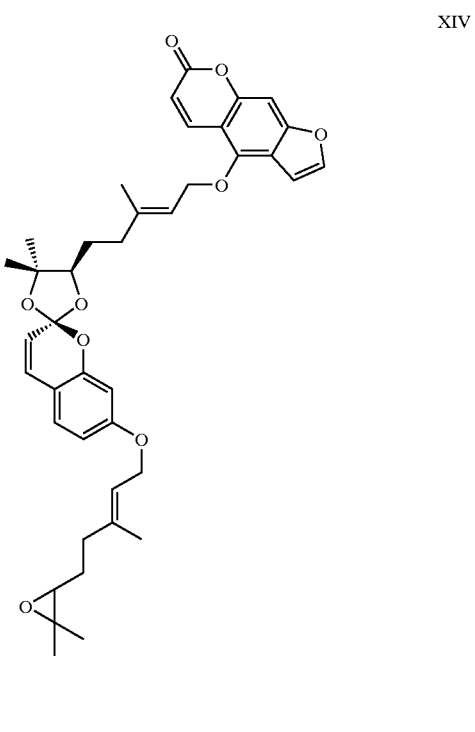
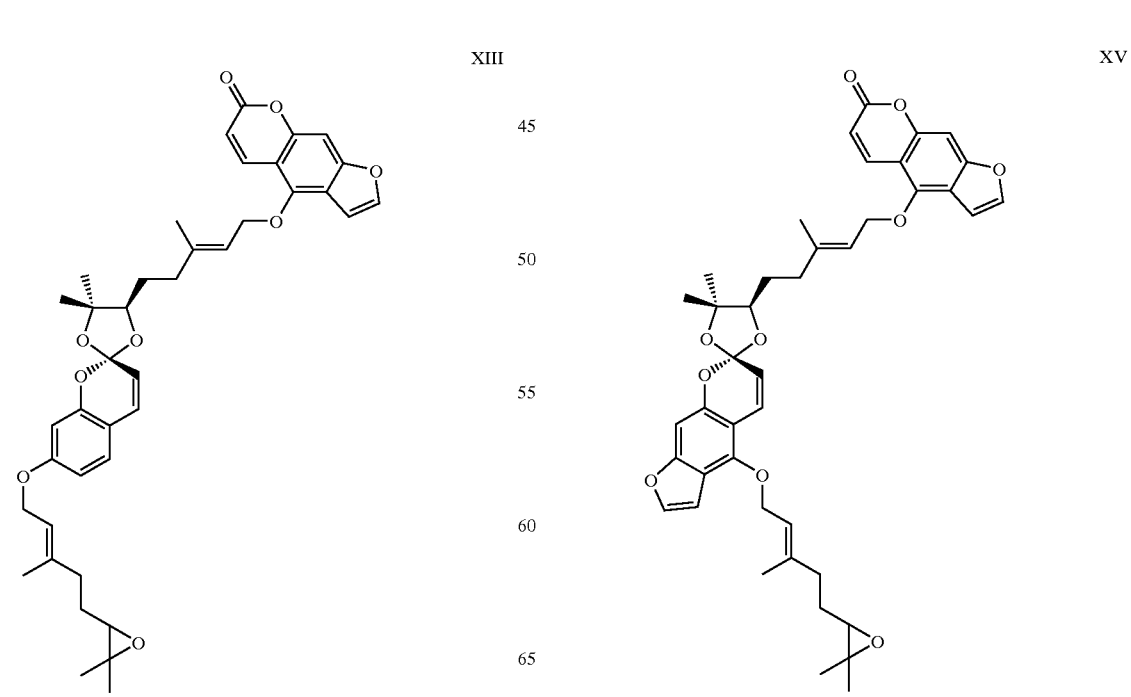

-continued

XVI

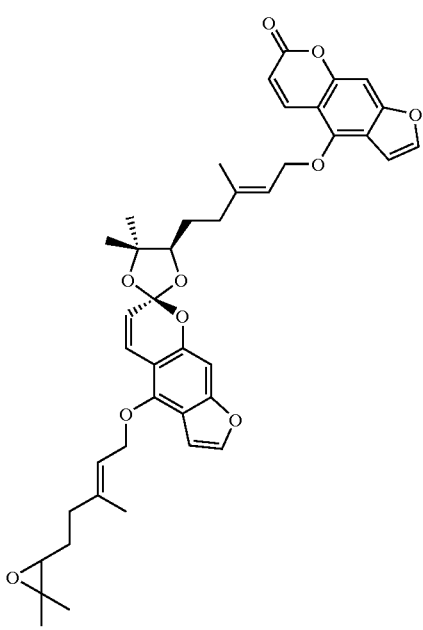

DETAILED DESCRIPTION OF THE PREFERRED EMBODIMENTS

Referring now to the drawings, wherein like reference numerals designate identical or corresponding chemicals throughout the reaction schemes.

The synthetic strategy of this invention is illustrated by the synthetic schemes shown in Scheme 1 and in FIGS. 1–3. The ortho esters and ortho carbonates available through the routes of Scheme 1 may be either cyclic or acyclic.

The transformation of a lactone to a cyclic ortho ester is carried out on Bergaptol ((2) in FIG. 1). The synthesis begins by generating the free phenol Bergaptol from Bergapten (1). Several routes are available to convert Bergapten (1) to Bergaptol (2). Reaction of Bergapten (1) in molten pyridine hydrochloride for 3 hours at 170° C. yields the Bergaptol in 94–96% yield (U.S. Pat. No. 4,217,445). The preferred route for demethylation is reaction of Bergapten (1) with 3.33 equivalents of $BCl_3$ in $CH_2Cl_2$ and 1.33 equivalents of $[Bu_4N]$ [I] at 0° (J. Org. Chem. 64(26) 9719–21 (1999)). The resulting reaction mixture was quenched in MeOH or EtOH, filtered, and rinsed with acetone.

Bergaptol (2) must be protected before further reaction. A variety of protecting groups may be used including TBDMS (t-butyldimethylsilyl), allyl, Bn (Benzyl), Ts (tosyl), TBDPS (t-butyldiphenylsilyl), TIPS (tri-iso-propylsilyl), 2-naphthyl, PMB (p-methoxybenzyl), SEM (—$CH_2OCH_2CH_2$-TMS), 4-nitrobenzyl, diphenyl phosphate, etc. Reacting Bergaptol (2) with the halide of the protecting group in, e.g., dimethylformamide (DMF) at 70° C. in the presence of a base followed by aqueous workup and extraction into ethyl acetate, or, for TBDMS, imidazole, at room temperature followed by quenching in EtOAc and precipitating by addition of hexane gave the protected Bergaptol (3) as a solid in good yield. Preferred protecting groups include TBDMS and Bn.

In a preferred embodiment the choice of protecting group is an important factor in isolating the cyclic ortho ester (4) in good yield. Preferred protecting groups have the following characteristics:

1. The protecting group should be able to withstand the alkylating agent, a strong base or a nucleophile.
2. The protecting group should be stable under conditions of the trans orthoesterification reaction.
3. Deprotection must be possible even after the ortho ester functionality has been generated.

Once protected, the carbonyl moiety of the lactone group is reacted with an alkylating agent. In the absence of a protecting group, an alkylating agent such as $[Me_3O][BF_4]$ transforms the hydroxyl of bergaptol to an ether linkage. Ethoxy substituted ortho esters are more stable and easier to isolate, however only low yields were achievable when $[Et_3O][BF_4]$ was used as the alkylating agent. Yields of the diethoxy ortho ester of protected bergaptol were difficult to control and varied from 10 to 30%. These yields were obtained with TBDMS as the protecting group and $[Et_3O][BF_4]$ as the alkylating agent followed by reaction with alkoxide.

While not bound by a particular theory, the low yields are thought to be caused by attack of the protecting group by alkoxide, or due to trace $F^-$ or $[BF_4]^-$.

Derivatives wherein the Bergaptol (2) is protected with tert-butyl diphenyl silyl or triisopropylsilyl groups did not lead to the isolation of the desired cyclic ortho ester when $[Et_3O][BF_4]$ was used. The protected Bergaptol is first alkylated at the carbonyl oxygen atom but, upon treatment with sodium ethoxide, deprotection occurs. Other protecting groups were also examined including 4-nitrobenzyl and diphenylphosphate. In neither case was it possible to obtain the cyclic ortho ester in isolatable yields.

Impurities in the alkylating agent were suspected as a cause of the poor yields. Reactions conducted in the presence of sodium carbonate indicated that acidic impurities present in the $[Et_3O][BF_4]$ preparation were not responsible for the low yield.

In comparison to the attempted synthesis of cyclic ortho esters using $[Et_3O][BF_4]$ as an alkylating agent, the use of $[Et_3O][PF_6]$ was much more effective in generating the cyclic ortho ester. For example, when the synthetic target was the diethoxy ortho ester of TBDMS-protected bergaptol, use of $[Et_3O][BF_4]$ gave an erratic 10–30% isolated yield while the use of $[Et_3O][PF_6]$ gave isolated yields that were consistently between 70–75%. This improvement in yield is quite surprising considering that the only change to the alkylating agent is the counter anion ($BF_4$ vs. $PF_6$). The robustness of the reaction is equally unexpected. The $[Et_3O][PF_6]$ was used as both fresh and aged solutions in $CH_2Cl_2$, and both solutions generated good yields. Experiments using the $[BF_4]^-$ salt required five equivalents of $[Et_3O][BF_4]$ per equivalent of protected Bergaptol (3). The corresponding $[PF_6]^-$ mediated reaction can be carried out with 2.0 equivalents of the alkylating agent and 2.0 equivalents of NaOEt with no adverse effect on yield. Use of the $[PF6]^-$ salt of the alkylating agent also allowed the purification procedure to be simplified. Passing the reaction solution, after aqueous work up and solvent removal, through $NEt_3$-deactivated silica gel or basic alumina resulted in the isolation of a spectroscopically pure product. In this sense, a preferred alkylating agent is $[Et_3O][PF_6]$. However, other [RO] [anion] pairs can be used where the anion is a non-coordinating ion that doesn't interfere with reaction chemistry and R is preferably $C_1$–$C_{20}$ alkyl. One other anion is $[SbF_6]^-$. Useful agents also include tri $C_{1-20}$ alkyl oxonium ion-anion pairs where the alkyl groups are the same or different and the anion is an anion of a halogenated (e.g., fluorinated) main group elements, or a group V hexafluoride. Preferably the agent does not comprise $[Et_3O][BF_4]$ or

[Et$_3$O] [SbCl$_6$], and more preferably does not comprise [BF$_4$] or [SbCl$_6$].

While not bound by a particular theory, the increased efficiency of the [PF$_6$]$^-$ counterion may be due to the enhanced stability of [PF$_6$]$^-$ relative to [BF$_4$]$^-$. Enhanced stability could result in fewer side reactions, and thus in a preferred embodiment relative stability should be considered in selecting the counterion.

The agent [Et$_3$O] [PF$_6$] and, more specifically, the counterion [PF$_6$]$^-$ has never been used for these transformations as evidenced by searches of the databases HCAPLUS, CAOLD, and CASREACT conducted by Chemical Abstracts Service personnel (CAS Client Services Order Number 61840, incorporated herein by reference). Of course, and as noted above, other agents such as [R$_3$O] [PF$_6$] may be used as well, alone or in mixture with [Et$_3$O] [PF$_6$], where R is C$_1$–C$_{25}$ linear, branched, cyclic, aromatic, etc. groups. Note also, Scheme 1 above where R$^{3(+)}$ and R$^{3'(+)}$ correspond to the Et$_3$O$^+$ portion of [Et$_3$O] [PF$_6$]. synthetic procedure using the [PF$_6$]$^-$ salt of the alkylating agent and benzyl protected Bergaptol (3) provided the cyclic ortho ester in yields of 75–80%. Comparative yields using the [BF$_4$]$^-$ salt are between 40 and 45%. The [PF$_6$]$^-$ alkylating agent is stable in CH$_2$Cl$_2$ solution for prolonged periods (8 weeks) at 0° under nitrogen without significant effect on yield. The use of the [PF$_6$]$^-$ reagent also allows use of less stringent reaction conditions. The yields obtained in reactions wherein the glassware was not dried in comparison to yields obtained when the glassware was pre-dried with a heat gun do not show any significant difference. Moreover, the [PF$_6$]$^-$ reagent solution may be stored at ambient temperature and atmosphere for short periods without a decrease in yield. The above-described ability of [PF$_6$]$^-$ mediated cyclic ortho ester-forming reactions to tolerate adventitious moisture and air exposure affords a distinct and surprising advantage of this technology over other known ortho ester-forming reactions.

The sensitivity of the reaction to the alkali metal of the alkoxide was tested by varying the alkali metal and solvent. Results obtained for the reaction of the TBDMS-protected Bergaptol (3) and 2.0 equivalents of [Et$_3$O] [PF$_6$] followed by two equivalents of ethoxide are shown in Table I.

TABLE I

| MOEt | Solvent | Yield (%) |
| --- | --- | --- |
| Li | TUF | 79 |
| Li | EtOH | 77 |
| Na | EtOH | 75 |
| K | EtOH | 74 |

Additional results, obtained by varying the solvent and the alkyl group of the alkoxide are shown in Table II. When a potent nucleophile such as K$^+$ or Cs$^+$ salt of methoxide is used low yields are typically obtained.

TABLE II

| MOR | R | Solvent | Yield (%) |
| --- | --- | --- | --- |
| Li | Me | MeOH | 77 |
| Na | Me | MeOH | 78 |
| K | Me | MeOH | 41 |
| Cs | Me | MeOH | 45 |
| Li | Et | THF | 79 |
| Li | Et | EtOH | 77 |
| Na | Et | EtOH | 75 |

TABLE II-continued

| MOR | R | Solvent | Yield (%) |
| --- | --- | --- | --- |
| K | Et | EtOH | 74 |
| Na | CH$_2$CH$_2$OMe | MeOCH$_2$CH$_2$OH | 72 |

The order of addition has little effect on the yields of the reaction when [PF$_6$]$^-$ is used as a counterion for the alkylating agent. This is surprising in view of the fact that when [BF$_4$]$^-$ is used as a counterion for the alkylating agent, none of the desired product is obtained upon 'reversal' of the order of addition. Reversal of the order of addition comprises adding the NaOEt to the alkylated-lactone intermediate, and this order of addition is advantageous because it is a simpler operation to conduct.

Cyclic ortho esters and cyclic ortho carbonates containing mixed alkoxy groups can also be obtained. A combination of higher volatility and greater electron deficiency are preferred in the alcohol (e.g., allyl, propargyl). The alkoxides of these alcohols can be obtained by reacting NaH with an excess of the corresponding alcohol. A mixed alkoxy ortho ester of protected Bergaptol (4) can be obtained in 81% yield by reaction of protected bergaptol (3) with [Et$_3$O] [PF$_6$] followed by reaction with sodium propargyloxide followed by filtration through basic alumina.

The PF$_6$-mediated reactions give surprisingly clean reaction products. Spiro ortho esters were obtained in a one-pot synthesis by reaction of protected Bergaptol (4), formed in situ, with the alkali metal salt of a diol. The alkylated Bergaptol is reacted with a slight excess of the diol alkoxide to give the spiro ortho ester which is then purified by passage through activated basic alumina. These data and experience are contrary to those cyclic ortho ester or cyclic ortho carbonate preparations that were too complex to afford an inexpensive purification (as has been the case with other ortho ester- or ortho carbonate-forming technologies; see, for example, U.S. Pat. No. 4,738,899). When [Et$_3$O] [PF$_6$] is used with either benzyl- or TBDMS-protected bergaptol, spectroscopically pure cyclic ortho esters are obtained by simple passage of the crude reaction mixture through a plug of activated basic alumina. Hence, if spiro ortho esters or spiro ortho carbonates are desired, they may be prepared with or without purification of the ortho ester or ortho carbonate intermediates.

This method of synthesis, when applied to the production of ortho esters and ortho carbonates, offers a synthetic route free of the toxicological and environmental risks associated with existing methods for preparing these chemicals. For example, U.S. Pat. No. 4,891,436 describes a process that requires the use of a tin intermediate or reaction bottoms from industrial alkyl chlorination processes. Similarly, U.S. Pat. No. 4,849,529 describes processes that use Lewis acids, some of which present significant waste disposal issues. These methods thus suffer from environmental and processing drawbacks and additionally afford the target ortho carbonates in only low to moderate yield.

The cyclic ortho ester (4) resulting from the alkylation was converted to the spiro ortho ester (6) by reaction with the alkylated Bergaptol derivative (5). The intermediate (5) may be prepared by reacting equimolar amounts of Bergaptol (2) with a geraniol derivative (22). The synthetic route to the alkylated Bergaptol (5) is schemed in FIG. 2.

Beginning with geraniol (20) as the starting material, conversion to the halogenated diol (22) was accomplished by protecting the hydroxyl, epoxidizing the 6,7 alkene, protecting the resulting diol, and finally deprotection and halogenation of the terminal alcohol.

The protected geranyl group is formed by reaction of geraniol with a protecting group. Any number of protecting groups can be used, including without limitation phenylacetyl, Cbz, TBDMS, TBDPS, TMS, pivaloyl, allyl, benzyl, benzoyl, and trityl. A preferred protecting group is 3,5-dinitrobenzoyl, and phenyl carbomoyl is particularly preferred.

The epoxidation of the geranyl phenylcarbonate was accomplished using an enatioselective epoxidation technique (PCT documents WO 98/15544 and WO 01/12616 incorporated herein by reference). Reaction of the carbonate with D-Epoxone (1, 2:4, 5, di-O-isopropylidine-b-D-erythro-2,3-hexodiulo-2,6-pyranose) in acetonitrile followed by a 1M aqueous potassium carbonate solution and finally by slow (2 hours) addition of 30% $H_2O_2$ at 25° C. led to the mono-epoxidated product that was converted to the corresponding diol by addition of a catalytic amount of perchloric acid in a THF/water solution. Recrystallization of the resulting oil gave the diol carbonate in 58% yield of a crystalline solid of 88% ee optical purity. Confirmation of the configuration of the diol carbonate (21) was obtained by comparing the optical rotation of the reaction product with known values (*J. Org. Chem.*, 54, 4686 (1989)).

The 6,7-dihydroxy geranyl N-phenyl carbonate can be resolved using an esterhydroxyase as an alternative to asymmetric epoxidation. Resolution of the diol with Chiro CLEC-PC in vinyl acetate allowed isolation of the (6S)-6, 7-dihydroxy geranyl N-phenyl carbonate in 78% ee optical purity. Inversion of the S enantiomer yields the desired R enantiomer. Procedures for inverting the hydroxyl are known in the art (*J. Org. Chem.*, 54, 4686 (1989)). Resolution can also be accomplished through resolution of the ester with phosphate, sulfate, or monoesters of dicarboxylic acids.

The diol carbamate (21) was protected as an acetonide by reaction of 2,2-dimethoxypropane (2,2-DMP) in the presence of p-toluene sulfonic acid at room temperature. The carbonate was then deprotected by reaction with a base in MeOH. Reaction with aqueous NaOMe in MeOH cosolvent is preferred. The hydroxyl (21, P=hydrogen) was converted to a halogenated derivative by reaction with a halogenating agent such as p-toluene sulfonyl chloride or $PBr_3$.

The alkylated Bergaptol product (5) was formed by reaction of the geranyl halide (22) with Bergaptol (2) in THF/DMF mixtures for 16 hours at 70° C. to provide (5) in greater than 50% isolated yield.

Reaction of the alkylated Bergaptol (5) with the cyclic ortho ester (4) was accomplished by using an equimolar or preferably slight molar excess of (5). The reaction takes place at room temperature in THF or EtOAc solvent in the presence of catalytic or stoichiometric amounts of PyTsOH. The release of EtOH during the course of this reaction interferes with completion of the reaction. Conducting the reaction in low boiling solvents under vacuum aids to remove EtOH as it is formed, thereby allowing more complete reaction and limiting the formation of side products (R. H. DeWolfe, *Carboxylic Ortho Acid Derivatives: Preparation and Synthetic Applications*, Academic Press, 1970, page 18; *Advances in Polymer Science*, Vol. 107, pp. 41–92, 1992).

In order to continue synthesis of the anti-first-pass effect compound (10), the reaction product (6) must be deprotected to allow for a second alkylation with the protected geraniol derivative (22A). Deprotection of (6) was accomplished with agents such as TBAF (for silyl protecting groups) or via transfer hydrogenation. When a Pd/carbon catalyst is used (e.g., benzyl protecting group) 1,4-cyclohexadiene (as the $H_2$ source) and acetic acid are preferred as hydrogen sources in THF solution.

Final alkylation involves combining the protected diol halide (22A) with the phenolic spiro ortho ester (7). The reaction was carried out at elevated temperature in the presence of $NEt_3$ and $K_2CO_3$ to yield the protected form of the desired spiro ortho ester diol (9). Deprotection of (9) generates the desired spiro ortho ester diol (10).

In view of the above description one of ordinary skill can prepare all the compounds described herein and other ortho esters and ortho carbonates by appropriate choice of ring structure, side chain, etc. of reactants. In this regard, temperatures can vary, and for example generally vary from −50° to 100° C., preferably −20° to 80° C. more preferably 0 to 70° C. Ratios of equivalents of reactants can vary, for example from 0.01–100, preferably 0.1–10, more preferably from 0.5–4. Time of reaction can be determined by employing analytical techniques to determine yield, purity, etc. Those of ordinary skill are capable of such work in view of the description above and the guidance provided by the non-limiting examples below.

Experimental Procedures

Bergapten (1) was purchased. Geraniol was obtained from Millennium Specialty Chemicals, Inc. [$Et_3O$]$PF_6$ was purchased from Aldrich and dissolved under a nitrogen atmosphere in enough anhydrous $CH_2Cl_2$ to form a 1 M stock solution, which is stored under nitrogen at 0° C. All other reagents were purchased from Aldrich or Fluka and used without further purification. All solvents were of Aldrich's "Sure-Seal" anhydrous grade. All column chromatography was carried out using silica gel (catalog number 22, 719-6; Merck, grade 60, 230–400 mesh, 60A°). Activated basic alumina is from Aldrich (catalog number 19,944-3; Brockmann I, standard grade, ~150 mesh, 58A°).

In order to analyze the chemical preparations disclosed herein, several high performance liquid chromatography (HPLC) methods were developed. The details of each method are listed below. HPLC Method One: Linear gradients are used for elution and are formed by mixing mobile phase A composed of water with mobile phase B composed of acetonitrile (instrument: Hewlett Packard). The elution time, in minutes, and the percentage of mobile phase B present in the mixed mobile phase are as follows: 0, 10; 5, 10; 30, 80; 40, 80; 41, 95; 50, 95; 53, 10; 68, 10. The flow rate is 0.2 mL/min throughout the run. The chromatographic column has dimensions of 150 mm length×2.1 mm internal diameter, is packed with a proprietary material (J'Sphere ODS-M80, 4 μM, YMC, Inc.), and is maintained at 35° C. The column eluate from each injection is monitored for absorbance at 244 nm and at 310 nm. HPLC Method Two: Linear gradients are used for elution and are formed by mixing mobile phase A composed of water with mobile phase B composed of acetonitrile (instrument: Hewlett Packard). Both the water and the acetonitrile contained 0.025% (v/v) trifluoroacetic acid. The elution time, in minutes, and the percentage of mobile phase B present in the mixed mobile phase are as follows: 0, 40; 12, 40; 13, 90; 25, 90; 40, 40. The flow rate is 0.2 mL/min throughout the run. The chromatographic column has dimensions of 150 mm length×2.1 mm internal diameter, is packed with a proprietary material (J'Sphere ODS-M80, 4 μM, YMC, Inc.), and is maintained at 35° C. The column eluate from each injection is monitored for absorbance at 244 nm and at 310 nm. HPLC Method Three: Isocratic elution is used, and the mobile phase is formed by mixing mobile phase A composed of 400 mL of 2,2,4-trimethylpentane and 20 mL of 2-propanol with mobile phase B composed of reagent alcohol (instrument: Hewlett Packard). The percentage of mobile phases A and B present in the mixed mobile phase is 75:25 throughout each run. The flow rate is 1.0 mL/min throughout the run. The chromatographic column has dimensions of 250 mm length×4.6 mm internal diameter, is packed with a proprietary material (Chiral DNB (S), 5 μM, Keystone Scientific), and is maintained at 40° C. The column eluate from each injection is monitored for absorbance at 245±8 nm. HPLC Method Four: Isocratic elution is used, and the mobile phase is formed by mixing 2-propanol into heptane in a 16.5:83.5 (v/v) ratio (instrument: Hewlett Packard). The flow rate is 1.0 mL/min throughout the run. The chromatographic column has dimensions of 250 mm length×4.6 mm internal diameter, is packed with a proprietary material (Chiralpak AD, 5 μM, Chiral Technologies/Daicel), and is maintained at 13° C. The column eluate from each injection is monitored for absorbance at 302 nm.

De-methylation of Bergapten 1 to Bergaptol 2

To a heat-gun dried flask fitted with a graduated addition funnel under nitrogen was added 25.9 g (120 mmol) of bergapten 1, 59 g (160 mmol; 1.33 equiv.) of [Bu$_4$N]I and 400 mL of anhydrous CH$_2$Cl$_2$. The resulting white slurry was immersed in an ice bath and the internal temperature monitored by a thermocouple. To the graduated addition funnel was added 400 mL of 1.0 M BCl$_3$ in CH$_2$Cl$_2$ ("smoking" during addition). The BCl$_3$ solution was added dropwise to the slurry over the course of 2 hours (internal temperature up to 3.7° C). After the addition was complete, the ice bath was removed and the reaction was allowed to warm to room temperature over the next 30 minutes. After stirring at room temperature for an additional 2 hours, the reaction mixture was quenched by pouring into 400 mL of MeOH with vigorous stirring over 10 minutes (exothermic quench). The resulting pale yellow slurry was stirred for 15 minutes to cool to room temperature. Filtration through a coarse fritted-funnel (~15 minutes) gave a pale yellow cake which was rinsed with 2×250 mL of acetone. After air-drying, 18.0 g (74% yield) of bergaptol 2 was obtained as a pale yellow powder. This procedure is based on *J. Org. Chem.*, 1999, 64(26), 9719–21.

1H NMR (300 MHz, d$_6$-DMSO) δ11.3 (br, 1H), 8.25 (d, 1H, J=9.7), 7.90 (d, 1H, J=2.1), 7.19 (d, 1H, J=2.9), 7.15 (s, 1H), 6.25 (d, 1H, J=9.7).

$^{13}$C NMR (75.4 MHz, d$_6$-DMSO) δ160.4, 157.0, 152.6, 147.9, 144.7, 139.6, 112.5, 110.7, 104.8, 103.7, 90.8. When HPLC Method Two was used, the elution time was 6.4 minutes.

General Procedure for the Synthesis of Silyl-protected Bergaptol 3a

To a heat-gun dried flask under nitrogen was added 100 mL of anhydrous DMF, 10.1 g of bergaptol 2 (50.0 mmol), 5.00 g of imidazole (73.4 mmol; 1.47 equiv.) and 11.0 g (72.8 mmol; 1.46 equiv.) of tertbutyl dimethylsilyl chloride (TBDMS-Cl). The resulting pale yellow solution was stirred at room temperature for 4 hours. The reaction was quenched by pouring into ~500 mL of EtOAc and rinsed with 8×100 mL of sat. NaCl. The ethyl acetate (EtOAc) phase was added to 100 mL of heptane and stripped of solvent to give a pale yellow solid. The pale yellow solid was rinsed with 3×100 mL of heptane to give 13.0 g (82% yield) of TBDMS-protected bergaptol 3a as a white solid after air drying.

1H NMR (300 MHz, CDCl$_3$) δ8.02 (d, 1H, J=9.8), 7.54 (d, 1H, J=2.4), 7.14 (s, 1H), 6.77 (d, 1H, J=2.4), 6.23 (d, 1H, J=9.8), 1.09 (s, 9H), 0.20 (s, 6H) ~10% disassociation observed in d$_6$-DMSO.

$^{13}$C NMR (75.4 MHz, CDCl$_3$) δ161.1, 157.6, 145.6, 144.8, 139.2, 116.9, 112.5, 108.2, 104.6, 94.3, 25.7, 18.4, −3.9. The TIPS (3c;) $^1$H NMR (300 MHz, CDCl$_3$) δ8.07 (d, 1H, J=9.8), 7.53 (d, 1H, J=2.4), 7.11 (s, 1H), 6.82 (d, 1H, J=2.4), 6.25 (d, 1H, J=9.8), 1.32 (m, 3H), 1.21 (d, 18H, J=6.9), TBDPS (3d;) $^1$H NMR (300 MHz, CDCl$_3$) δ8.30 (d, 1H, J=9.8), 7.70 (d, 4H, J=8.1), 7.36 (m, 6H), 7.06 (m, 2H), 6.25 (d, 1H, J=9.8), 5.93 (d, 1H J=2.4), 1.14 (s, 9H) and THDMS (3e; 1092–122) $^1$H NMR (300 MHz, d$_6$-DMSO) δ7.99 (m, 2H), 7.36 (s, 1H), 6.89 (d, 1H, J=2.3), 6.35 (d, 1H, J=9.8), 1.81 (m, 1H), 1.03 (s, 6H), 0.94 (d, 6H, J=6.9), 0.18 (2, 6H).

Other silyl derivatives are prepared via an analogous method; however, it may be necessary to pass the pale yellow solid though a plug of silica gel to remove residual silicon containing species.

Synthesis of Benzyl-protected Bergaptol 3b

To a heat-gun dried flask fitted with a reflux condenser and under nitrogen was added 50 mL of anhydrous DMF, 200 mL of anhydrous THF, 6 mL (50.5 mmol; 1.01 equiv.) of benzyl bromide, 10.1 g (50 mmol) of bergaptol 2 and 13.8 g (100 mmol; 2.00 equiv.) of K$_2$CO$_3$. The resulting brown slurry was immersed in an oil bath and heated to 70° C. Internal temperature monitoring indicated that an exothermic event occurred at around ~60° C. (the internal temperature reached 73° C. while the bath temperature remained at around 63–64° C.). After stirring at 70° C. for 16 hours, the reaction was allowed to cool to room temperature. The reaction mixture was passed through a coarse fritted-funnel to remove the insoluble inorganic salts. The resulting olive-green solution was stripped of solvent by a rotary evaporator at 50° C. to give a green semi-solid. The semi-solid was rinsed sequentially with 3×100 mL of heptane, 5×150 mL of sat. NaHCO$_3$ and 3×200 mL of H$_2$O. The resulting paste was suspended in 150 mL of toluene dried via a rotary evaporator. The resulting gray solid was suspended in ~150 mL of EtOAc and heated till a homogeneous dark green solution was achieved (~65° C.). Precipitation began to form as the solution cooled to room temperature. After cooling to room temperature, the flask was stored at 0° C. for another hour. The gray precipitate was collected on a flitted-funnel and rinsed with 3×100 mL of heptane to give 11.7 g of benzyl-protected bergaptol 3b. The mother liquor was stripped of solvent and recrystallized from ~75 mL of EtOAc to obtain an additional 1.2 g of benzyl-protected bergaptol 3b as a gray solid. The total yield is 12.9 g (88%).

Synthesis of Bergamottin 3f

To a heat-gun dried flask fitted with a condenser and under nitrogen was added 10 mL of anhydrous DMF, 40 mL of anhydrous THF, 2 mL (10.1 mmol; 1.01 equiv.) of geranyl bromide, 2.02 g (10.0 mmol) of bergaptol 2 and 1.64 g (20.0 mmol; 2.00 equiv.) of NaOAc The resulting yellow solution was immersed in an oil bath and heated to 70° C. After stirring at 70° C. for 16 hours, the reaction was allowed to cool to room temperature. The reaction was quenched with 50 mL of 1 N NaOH and extracted with 200 mL EtOAc. The organic phase was rinsed with 1 N NaOH (5×50 mL) followed by sat. NaCl (1×50 mL). The organic layer was dried with MgSO$_4$, filtered, and stripped of solvent. Column chromatography (10% EtOAc/90% hexanes) gave 283 mg of the bis-alkylated product 3g where the carbon para to the alkylated hydroxy is also alkylated as a pale yellow solid (R$_f$~0.3; 12% yield) and 2.26 g of bergamottin 3f as a white solid (R$_f$~0.2; 61% yield). The reaction was successfully scaled up to 140 mmol scale; however, the 3f/3g ratio was not determined. Geranyl chloride can be used instead of geranyl bromide to give analogous result (10% 3g/57% 3f).

This alkylation is described in literature using different conditions, see: F. H. Bellevue III and P. M. Woster *Bioorg.*

*Med. Chem.* 20, 2593 (1997) and D. J. Edwards and P. M. Woster PCT application WO 98/17667.

3g: $^1$H NMR (300 MHz, CDCl$_3$) δ8.15 (d, 1H, J=9.9), 7.61 (d, 1H, J=2.3), 6.93 (d, 1H, J=2.3), 6.26 (d, 1H, J=9.9), 5.53 (t, 1H, J=6.8), 5.35 (t, 1H, J=6.9), 5.06 (m, 2H), 4.87 (d, 2H, J=6.8), 3.74 (t, 2H, J=6.9), 2.02 (m, 8H), 1.87 (s, 3H), 1.67 (s, 6H), 1.53 (s, 9H). $^1$H NMR (300 MHz, C$_6$D$_6$) δ7.96 (d, 1H, J=9.8), 7.00 (d, 1H, J=2.3), 6.47 (d, 1H, J=2.3), 5.63 (d, 1H, J=9.9), 5.47 (t, 1H, J=6.8), 5.12 (t, 1H, J=6.9), 5.09 (m, 2H), 4.55 (d, 2H, J=2H, J=6.8), 3.85 (t, 2H, J=6.9), 2.01 (m, 8H), 1.97 (s, 3H), 1.66 (s, 3H), 1.58 (s, 3H), 1.53 (s, 3H), 1.46 (s, 3H), 1.43 (s, 3H), 1.52 (s, 3H). $^1$H NMR (300 MHz, d$_6$-DMSO) δ8.18 (d, 1H, J=9.8), 8.04 (d, 1H, J=2.3), 7.28 (d, 1H, J=2.3), 6.31 (d, 1H, J=9.9), 5.49 (t, 1H, J=6.8), 5.24 (t, 1H, J=6.9), 4.96 (m, 4H), 3.61 (d, 2H, J=6.9), 1.95 (m, 8H), 1.81 (s, 3H), 1.66 (s, 3H), 1.62 (s, 3H), 1.56 (s, 3H), 1.50 (s, 3H), 1.45 (s, 3H). $^{13}$C NMR (75.4 MHz, CDCl$_3$) δ160.8, 156.4, 149.3, 146.5, 144.5, 142.2, 139.3, 136.1, 131.5, 130.8, 124.0, 123.4, 120.6, 119.0, 113.7, 111.9, 109.4, 104.9, 69.6, 39.4, 39.2, 26.3, 25.9, 25.3, 25.2, 21.8, 17.4, 17.3, 16.3, 15.9. When HPLC Method One was used, the elution time was 56.5 minutes. When HPLC Method Three was used, the elution time was 4.3 minutes.

3f: $^1$H NMR (300 MHz, CDCl$_3$) δ8.15 (d, 1H, J=9.6), 7.59 (d, 1H, J=2.1), 7.15 (s, 1H), 6.95 (d, 1H, J=2.1), 6.26 (d, 1H, J=9.6), 5.53 (t, 1H, J=6.8), 5.07 (m, 1H), 4.94 (d, 2H, J=6.8), 2.09 (m, 4H), 1.69 (s, 3H), 1.67 (s, 3H), 1.59 (s, 3H). $^1$H NMR (300 MHz, d$_6$-DMSO) δ8.17 (d, 1H, J=9.8), 8.05 (s, 1H, J=2.3), 7.38 (s, 1H), 7.36 (d, 1H, J=2.3), 6.32 (d, 1H, J=9.8), 5.51 (t, 1H, J=6.6), 5.00 (m, 3H), 2.00 (m, 4H), 1.64 (s, 3H), 1.60 (s, 3H), 1.53 (s, 3H). $^{13}$C NMR (75.4 MHz, CDCl$_3$) δ160.8, 157.8, 152.3, 148.7, 144.5, 142.6, 139.2, 131.6, 123.3, 118.7, 113.7, 112.0, 107.0, 104.8, 93.6, 69.4, 39.1, 26.0, 25.4, 17.4, 16.3. When HPLC Method One was used, the elution time was 40.9 minutes. When HPLC Method Three was used, the elution time was 6.7 minutes.

Synthesis of 6,7-dihydroxybergamottin 5

The synthesis of compound 5 from bergamottin 3f is described in literature, see: F. H. Bellevue III and P. M. Woster *Bioorg. Med. Chem.* 20, 2593 (1997) and D. J. Edwards and P. M. Woster PCT application WO 98/17667.

Synthesis of Racemic 6,7-epoxybergamottin 3h

To a flask under air was added 2.30 g (6.80 mmol) of bergamottin 3f and 20 mL of CH$_2$Cl$_2$. The resulting pale yellow solution was cooled to 0° C. in an ice bath. To this chilled solution was added dropwise over 30 minutes a cold (0° C.) solution of 1.55 g (5.02–7.71 mmol; 0.738–1.13 equiv.) of 56–86% m-CPBA (remainder is the corresponding carboxylic acid; used as received, exact concentration not determined) in 15 mL of CH$_2$Cl$_2$. After the complete addition of m-CPBA, the resulting cloudy slurry was stirred at 0° C. for an additional 30 minutes. The reaction was then poured into 150 mL of EtOAc and rinsed alternatively with sat. NaHCO$_3$ and 0.1 N Na$_2$S$_2$O$_7$ (5×50 mL each) followed by a final rinse with 50 mL of sat. NaCl. The organic layer was dried with MgSO$_4$ and stripped of solvent. Column chromatography (25% EtOAc/75% hexanes; R$_f$~0.25) gave 2.13 g (88% yield) of rac. 3h as a white solid.

Synthesis of Racemic 6,7-dihydroxybergamottin

To a flask under air was added 2.00 g (5.65 mmol) of the epoxide rac. 3h, 20 mL of THF and 0.5 mL (~0.15 mmol; ~3 mol %) of 3% aqueous HClO$_4$. The resulting clear colorless solution was stirred at room temperature. After 30 minutes, the reaction mixture was poured into 50 mL of EtOAc and rinsed with sat. NaHCO$_3$ 1×20 mL followed by sat. NaCl 1×20 mL. The organic layer was dried with MgSO$_4$ and stripped of solvent. Column chromatography (2:1 EtOAc/hexanes; R$_f$~0.4) gave 1.56 g (74% yield) of rac. 5 as a white solid.

Asymmetric Synthesis of (R)-6,7-dihydroxybergamottin (R)-5

To a flask immersed in a 0° C. bath was added 150 mL t-BuOH, 150 mL water, 30 g of AD-Mix-β (equivalent to 30 mmol) and 2.85 g of MeSO$_2$NH$_2$ (30.0 mmol; 1.00 equiv.). To the resulting orange slurry was added 10.1 g of bergamottin 3f (29.9 mmol), not all of which dissolved initially. The resulting orange/white slurry was stirred at 0° C. for 16 hours and then quenched with approx. 45 g of Na$_2$SO$_3$ at 0° C. The quenched reaction mixture was warmed to room temperature over 30 minutes, poured into 500 mL of EtOAc and the phases were separated. The aqueous layer was extracted with EtOAc (3×100 mL). All EtOAc extraction solutions were combined and rinsed with 2 N NaOH (4×100 mL) followed by sat. NaCl (3×100 mL). The organic layer was dried with MgSO$_4$, filtered and stripped of solvent. Column chromatography (60% EtOAc/40% hexanes; Rf~0.2) gave 5.61 g (51% yield) of (R)-5 as a white solid. Chiral HPLC determined the optical purity of (R)-5 thus obtained to be 96% ee and the absolute configuration to be (R).

Alternatively, this compound can be synthesized via asymmetric epoxidation using the, methodology described in literature (see Z.-X. Wang and Y. Shi *J. Org. Chem.* 63, 3099 (1998)) and subsequent ring opening as described in the synthesis of 5.

$^1$H NMR (300 MHz, CDCl$_3$) δ8.18 (d, 1H, J=9.8), 7.61 (d, 1H, J=2.4), 7.17 (s, 1H), 6.95 (d, 1H, J=2.4), 6.28 (d, 1H, J=9.8), 5.60 (t, 1H, J=5.5), 4.95 (d, 2H, J=5.5), 3.34 (m, 1H), 2.37 (m, 1H), 2.17 (m, 2H), 1.82 (s, 1H), 1.72 (s, 3H), 1.59 (m, 1H), 1.46 (m, 1H), 1.21 (s, 3H), 1.17 (s, 3H). $^1$H NMR (300 MHz, d$_6$-DMSO) δ8.18 (d, 1H, J=9.8), 8.04 (d, 1H, J=2.4), 7.37 (s, 1H), 7.33 (d, 1H, J=2.4), 6.32 (d, 1H, J=9.8), 5.54 (t, 1H, J=5.9), 5.00 (d, 2H, J=5.5), 4.28 (d, 1H, J=5.8), 3.30 (m, 1H), 2.22 (m, 1H), 1.98 (m, 1H), 1.65 (m, 1H) 1.63 (s, 1H), 1.23 (m, 1H), 1.03 (s, 3H), 0.98 (m, 3H) no nOe between italic signals. $^1$H NMR (300 MHz, CD$_3$OD) δ8.25 (d, 1H, J=9.8), 7.77 (d, 1H, J=2.4), 7.16 (s, 1H), 7.14 (d, 1H, J=2.4), 6.25 (d, 1H, J=9.8), 5.59 (t, 1H, J=5.5), 5.02 (d, 2H, J=5.5), 3.19 (m, 1H), 2.31 (m, 1H), 2.08 (m, 1H), 1.72 (m, 1H), 1.71 (s, 3H), 1.36 (m, 1H), 1.14 (s, 3H), 1.03 (s, 3H). When HPLC Method One was used, the elution time was 27.4 minutes. When HPLC Method Two was used, the elution time was 11.5 minutes. When HPLC Method Three was used, the elution time was 11.6 minutes. When HPLC Method Four was used, the elution time was 32.4 and 37.6 minutes.

General Procedure for the Synthesis of Dialkoxy-orthoesters 4a and 4b

To a heat-gun dried vial and under nitrogen was added 10 mmol of the protected bergaptol and 20 mL (20 mmol; 2.0 equiv.) of 1 M [Et$_3$O]PF$_6$ in CH$_2$Cl$_2$ to give a pale yellow solution which gradually turned into a slurry over the next 2 hours. After stirring at room temperature for 16 hours, the vial was immersed in an ice bath and the slurry was added dropwise over 5 minutes to 2.0 equiv. of alkoxide solution at 0° C. The resulting orange solution (or slurry, depending on substrate and/or the nature of the alkoxide) was stirred at 0° C. for 30 minutes and then poured into 300 mL of 95:5 EtOAc/NEt$_3$. After the organic phase was rinsed with 50 mL of sat. NaCl, it was concentrated to approx. 20 mL on a rotary evaporator. The concentrated organic phase was immediately passed through a 3"×3" plug of activated basic alumina and eluted with 500 mL solvent mixture (5:10:85, v:v:v, NEt$_3$/EtOAc/heptane). After solvent removal, the dialkoxy-orthoester is obtained as a colorless to pale yellow oil in 70–80% yield.

For the silyl-protected orthoesters, the initially clear to pale yellow oil darkened to pink-purple upon standing at room temperature, even when placed under vacuum. On a small scale (1 mmol) we found the order of addition is irrelevant (i.e., addition of the alkoxide solution to the slurry gave the same result).

4b (P=Bn): $^1$H NMR (300 MHz, d$_6$-DMSO) δ7.78 (d, 1H, J=2.3), 7.00 (d, 1H, J=9.4), 6.91 (s, 1H), 6.74 (d, 1H, J=2.3), 5.75 (d, 1H, J=9.4), 3.57 (q, 4H, J=7.1), 1.04 (t, 6H, J=7.1), 1.00, (s, 9H), 0.13 (s, 6H).

4a (P=TBDMS): $^1$H NMR (300 MHz, CDCl$_3$) δ7.36–7.46 (m, 6H), 7.22 (d, 1H, J=10.1), 6.90 (s, 1H), 6.78 (d, 1H, J=2.4), 5.64 (d, 1H, J=10.1), 5.30 (s, 2H), 3.66 (q, 4H, J=5.1), 1.22 (t, 6H, J=5.1). $^1$H NMR (300 MHz, d$_6$-DMSO) δ7.86 (d, 1H, J=2.3), 7.19–7.47 (m, 5H), 7.19 (d, 1H, J=2.4), 7.10 (d, 1H, J=10.0), 6.95 (s, 1H), 6.78 (d, 1H, J=2.4), 5.74 (d, 1H, J=10.1), 5.40 (s, 2H), 3.60 (q, 4H, J=5.1), 1.09 (t, 6H, J=5.1). When HPLC Method Three was used, the elution time was 4.3 minutes.

General Procedure for the Synthesis of O-protected Spiro-orthoesters 6a and 6b

To a heat-gun dried flask and under nitrogen was added 3.00 g (8.06 mmol; 1.01 equiv.) of (R)-6,7-dihydroxy bergamottin (R)-5, 300 mg (1.3 mmol; 15 mol %) of PyTsOH and 20 mL of anhydrous toluene. The resulting white slurry was stripped of solvent under vacuum for azeotropic drying. The diethoxy-orthoester (8.01 mmol) was dissolved in 20 mL of distilled THF and added to the dried diol and acid to give an orange solution. The progress of the reaction was monitored by TLC until the diethoxy-orthoester disappeared. For the TBDMS-protected diethoxy-orthoester, it is necessary to place the reaction under vacuum every 30–60 minutes to remove the released EtOH (along with THF). The resulting viscous foam was re-dissolved in distilled THF and another aliquot of PyTsOH added (the cycle repeated 3 times). The reaction was worked-up by pouring into 50 mL of EtOAc and rinsed with sat. NaCl (2×30 mL). Silica gel (5–10 g) was added to the EtOAc phase and the resulting slurry was stripped of solvent under vacuum to absorb the crude product onto silica gel. Column chromatography on NEt$_3$-deactivated silica gel using 5:20:75 NEt$_3$/EtOAc/hexane (benzyl R$_f$ ~0.2; TBDMS R$_f$ ~0.4) gave the desired O-protected spiro-orthoester in 60–65% yield for the benzyl-protected spiro-orthoester and 50–55% for the TBDMS-protected spiro-orthoester (30–35% if no solvent exchange via vacuum) as a white to pale yellow foam.

6a: $^1$H NMR (300 MHz, d$_6$-DMSO) δ8.19 (minor, d, 1H, J=9.7), 8.15 (major, d, 1H, J=9.7), 8.02 (major and minor, d, 1H, J=2.4), 7.77 (major and minor, d, 1H, J=2.4), 7.36 (major and minor, s, 1H), 7.30 (major and minor, d, 1H, J=2.4), 6.99 (major, d, 1H, J=10.1), 6.94 (minor, d, 1H, J=10.1), 6.81 (major and minor, s, 1H), 6.75 (major and minor, d, 1H, J=2.1), 6.32 (minor, d, 1H, J=9.8), 6.29 (major, d, 1H, J=9.8), 5.65 (major, d, 1H, J=9.9), 5.62 (minor, d, 1H, J=9.9), 5.53 (major and minor, t, 1H, J=5.8), 4.98 (major and minor, d, 2H, J=7.0), 4.08 (major, dd, 1H, J=3.6, 9.2), 3.76 (minor, dd, 1H, J=3.7, 9.9), 2.06–2.15 (major and minor, m, 2H), 1.64 (major and minor, s, 3H), 1.53–1.64 (major and minor, m, 2H), 1.36 (major and minor, s, 3H), 1.4 (major and minor, s, 9H), 1.03 (major, s, 9H), 0.16 (minor, s, 6H).

When HPLC Method Two was used, the elution time was 32.6 minutes. When HPLC Method Three was used, the elution time was 10.7 minutes.

6b: $^1$H NMR (300 MHz, d$_6$-DMSO) δ8.19 (minor, d, 1H, J=9.5), 8.17 (major, d, 1H, J=9.4), 8.06 (major and minor, d, 1H, J=2.4), 7.86 (major and minor, d, 1H, J=2.4), 7.32–7.52 (major and minor, m, 6H), 7.18 (major and minor, m, 1H), 7.09 (major, d, 1H, J=9.9), 7.07 (minor, d, 1H, J=9.9), 6.86 (major and minor, m, 1H), 6.33 (minor, d, 1H, J=9.8), 6.32 (major, d, 1H, J=9.8), 5.64 (major, d, 1H, J=9.9), 5.61 (minor, d, 1H, J=9.9), 5.56 (major and minor, t, 1H, J=6.8), 5.41 (major and minor, s, 2H), 5.02 (major and minor, d, 2H, J=7.0), 4.12 (major, dd, 1H, J=3.3, 9.2), 3.79 (minor, dd, 1H, J=3.2, 10.3), 2.13 (major and minor, m, 2H), 1.67 (major and minor, s, 3H), 1.57 (major and minor, m, 2H), 1.38 (major, s, 3H), 1.36 (minor, s, 3H), 1.12 (major and minor, s, 3H). When HPLC Method One was used, the elution time was 47.2 minutes. When HPLC Method Two was used, the elution time was 25.8 minutes. When HPLC Method Three was used, the elution time was 22.0 and 23.3 minutes.

Deprotection of the Benzyl-protected Spiro-orthoester 6b

To a vial under nitrogen was added 100 mg (0.155 mmol) of the benzyl-protected spiro-orthoester 6b, 75 mg (0.015 mmol; 10 mol %) of 5 wt % Pd/C (57.45 wt % H$_2$O Johnson Matthey catalog number A503038; lot number 545520), 1.5 mL of anhydrous THF, 30 mL (0.525 mmol; 3.39 equiv.) of acetic acid and 75 mL (0.793 mmol; 5.12 equiv.) of 1,4-cyclohexadiene. The resulting black slurry was stirred at room temperature for 30 minutes. After filtering off the Pd/C via an Acro-disc, the crude reaction mixture was subjected to chromatographic purification. Column chromatography (2:1 heptane/EtOAc; R$_f$~0.3) gave 38 mg (43% yield) of the free-phenol spiro-orthoester 7 as a white foam. Using 50 mg (0.792 mmol; 5.11 equiv.) of ammonium formate as the hydrogen source in the absence of acetic acid under otherwise identical conditions gave 20 mg (23% yield) of the product 7. It is likely that some of the free-phenol spiro-orthoester formed was converted to the ammonium salt was therefore not eluted by column chromatography.

$^1$H NMR (300 MHz, d$_6$-DMSO) δ10.3 (br, 1H), 8.19 (minor, d, 1H, J=9.8), 8.17 (major, d, 1H, J=9.8), 8.05 (major and minor, d, 1H, J=2.4), 7.68 (major and minor, d, 1H, J=2.4), 7.38 (major and minor, s, 1H), 7.34 (minor, d, 1H, J=2.4), 7.32 (major, d, 1H, J=2.4), 7.14 (major, d, 1H, J=9.9), 7.10 (minor, d, 1H, J=9.9), 7.02 (major and minor, s, 1H), 6.61 (major and minor, s, 1H), 6.33 (minor, d, 1H, J=9.8), 6.29 (major, d, 1H, J=9.8), 5.55 (major and minor, m, 2H), 5.00 (major and minor, d, 2H, J=7.0), 4.09 (major, dd, 1H, J=3.3, 9.0), 3.76 (minor, dd, 1H, J=3.4, 9.9), 2.00–2.20 (major and minor, m, 2H), 1.67 (major and minor, s, 3H), 1.50–1.70 (major and minor, m, 2H), 1.38 (major, s, 3H), 1.36 (minor, s, 3H), 1.11 (major and minor, s, 3H). When HPLC Method One was used, the elution time was 37.1 minutes. When HPLC Method Two was used, the elution time was 22.0 minutes. When HPLC Method Three was used, the elution time was 28.6 and 32.1 minutes.

De-silylation of the TBDMS-protected Spiro-orthoester 6a

To a flask immersed in an ice bath was added 850 mg (1.27 mmol) of the TBDMS-protected-spiro-orthoester 6a in 6 mL of THF. To this chilled colorless solution was added dropwise 1.4 mL (1.4 mmol, 1.10 equiv.) of 1 M tetrabutylammonium fluoride (TBAF) in THF, resulting in a yellow solution immediately. After stirring for 30 minutes at 0° C., the reaction was poured into 20 mL EtOAc and rinsed sequentially with 10 mL of 1 N HCl and twice with 20 mL of sat. NaCl. Solvent removal followed by column chromatography (2:1 hexane/EtOAc; R$_f$~0.2) gave 624 mg (88% yield) of the free-phenol spiro-orthoester 7 as a white foam.

Synthesis of (R)-12

R=acetyl

Via ketone reduction: M. Kamber and H. Pfander *Helv. Chim. Acta* 67, 968 (1984).

Via Sharpless dihydroxylation: E. J. Corey, M. C. Noe and W-C. Shieh *Tetrahedron Lett.* 34, 5995–5998 (1993).

R=acetyl or benzyl

Via ketone reduction: M. Kodama, H. Minami, Y. Mima and Y. Fukuyama *Tetrahedron Lett.* 31, 4025 (1990).

Synthesis of (S)-12

R=N-phenylcarbamoyl

J. D. Fourneron, A. Archelas and R. Furstoss *J. Org. Chem.* 54, 4686 (1989).

Synthesis of (R)-12 and (S)-12

R=acetyl or H

W. Eschenmoser, P. Uebelhart and C. H. Eugster *Helv. Chim. Acta* 66, 82 (1983).

R=N-phenylcarbamoyl

X. M. Zhang, A. Archelas and R. Furstoss *J. Org. Chem.* 56, 3814 (1991).

Synthesis of (S)-13

R=N-phenylcarbamoyl

J. D. Fourneron, A. Archelas and R. Furstoss *J. Org. Chem.* 54, 4686 (1989).

Conversion of (S)-13 into (S)-14

R=N-phenylcarbamoyl

J. D. Fourneron, A. Archelas and R. Furstoss *J. Org. Chem.* 54, 4686 (1989).

General papers on N-phenylcarbonate hydrolysis

M. Stankovicova, J. Cizmarik and Z. Bezakova *Pharmazie* 52, 881 (1997).

J. Berner *Z. Chem.* 22,221(1982).

Synthesis of (S)-14

H. Meier, P. Uebelhart and C. H. Eugster *Helv. Chim. Acta* 69, 106 (1986).

Synthesis of (S)-14 and conversion into (S)-8a

K. Mori and H. Mori *Tetrahedron* 43, 4097 (1987)

R. Schwabe, I. Farkas and H. Pfander *Helv. Chim. Acta* 71, 292 (1988).

Asymmetric epoxidation of geranyl derivatives

Z-X. Wang and Y. Shi *J. Org. Chem.* 63, 3099 (1998).

Protection of geraniol 68 mL (400 mmol) geraniol were dissolved in 36 mL (440 mmol) pyridine, cooled to 5° C. and 48 mL (440 mmol) phenylisocyanate were added dropwise maintaining an internal temperature of 20° C. The mixture was stirred at room temperature for 12 hours, 200 mL MTBE and 140 mL 10% HCl were added and the phases were separated. The organic layer was extracted against 100 mL 10% HCl, dried over sodium sulfate and the solvent removed by distillation. The residue was filtered through a silica gel pad and washed with heptane. The solvent was evaporated and the residue was dried in high vacuum leading to 96.7 gm (88%) geranyl N-phenylcarbonate as a yellow oil. The crude material was used without further purification.

6,7-Dihydroxygeranyl N-phenylcarbonate 12 (R=N-phenylcarbonate)

27.34 g (100 mmol) geranyl N-phenylcarbonate were dissolved in 200 mL dichloromethane, 200 mL saturated sodium bicarbonate solution were added and the biphasic mixture was cooled under stirring to 5° C. At this temperature a solution of 24.65 g (100 mmol) meta-chloroperbenzoic acid (mCPBA) in 250 mL dichloromethane was added dropwise maintaining an internal temperature of 10° C. After the addition was completed the mixture was stirred for 12 hours at room temperature. The phases were separated, the organic phase tested for peroxide and dried over sodium sulfate. The solvent was removed by distillation leading to the crude 6,7-epoxide of geranyl N-phenyl carbonate. The crude epoxide was dissolved in 330 mL THF and 50 mL water. 1 mL 70% perchloric acid was added and the mixture was stirred for 1 hour at room temperature. 250 mL ethyl acetate and 250 mL sat. sodium bicarbonate solution were added and the phases were separated. The organic layer was dried over sodium sulfate and the solvent was removed leading to a yellow oil. 330 mL toluene were added, the mixture was heated to reflux and upon cooling to room temperature the diol product precipitated. The solid was filtered and dried in high vacuum leading to 21.97 gm (72%) of 6,7-dihydroxygeranyl N-phenylcarbonate as a colorless solid.

Synthesis of 6,7-dihydroxygeranyl N-phenylcarbonate acetonide 13 (R=N-phenylcarbonate)

1.54 g (5 mmol) 12 (R=N-phenylcarbonate) were dissolved in 20 mL 2,2-dimethoxypropane (2,2-DMP). 76 mg (0.4 mmol) p-toluenesulfonic acid monohydrate (p-TsOH) were added and the mixture was stirred for 1 hour at room temperature. 2 mL sat. sodium bicarbonate solution were added, stirred for 30 minutes, 30 mL ethyl acetate and 5 mL water were added and the phases were separated. The organic layer was dried over sodium sulfate. The solvent was removed by distillation leading to 1.7 g of the acetonide as a light yellow oil (98% yield).

Synthesis of 6,7-dihydroxygeraniol acetonide 14

1.7 g (4.9 mmol) acetonide 13 (R=N-phenylcarbonate) were dissolved in 50 mL methanol. 50 mL 10% sodium hydroxide solution were added and the biphasic mixture is heated to 70° C. under stirring for 6 hours. The methanol was removed by distillation and the remaining aqueous layer was extracted twice with 50 mL heptane. The combined organic layer was dried over sodium sulfate, the solvent removed and the remaining liquid dried in high vacuum leading to 1 gm 14 (89% yield).

Synthesis of acetonide-protected 6, 7 dihydroxy geranyl bromide 8a 1 gm (4.4 mmol) alcohol 14 were dissolved in 20 mL MTBE and cooled to 0° C. At this temperature 0.5 mL (5.2 mmol) phosphor(III)bromide were added and the solution is stirred for 30 minutes. 30 mL sat. sodium bicarbonate solution were added, the biphasic mixture stirred for 30 minutes and the phases were separated. The organic layer was dried over sodium sulfate, the solvent was removed and the remaining oil was dried in high vacuum leading to 1 gm of the crude bromide 8a (75% yield). This material was used for the alkylation without further purification.

Alkylation of the free-phenol spiro-orthoester 7 with acetonide-protected geranyl-6,7-diol side chain 8a To a heat-gun dried vial under nitrogen was added 400 mg (0.719 mmol) of the free-phenol spiro-orthoester 7, 300 mg (2.17 mmol; 3.02 equiv.) $K_2CO_3$, 3 mL of distilled THF, 400 mg (1.37 mmol, 1.91 equiv.) of acetonide-protected 6,7-dihydroxy geranyl bromide 8a and 100 mL (0.719 mmol; 1.0 equiv) of $NEt_3$. The resulting slurry was heated at 50° C. for 24 hours. The reaction was quenched by pouring into 50 mL of EtOAc and rinsed sequentially with 20 mL of sat. $NaHCO_3$ followed by 20 mL of sat. NaCl. After solvent removal and column chromatography (30% EtOAc; $R_f$~0.3), the desired O-alkylated spiro-orthoester 9a was obtained in ~40% yield (252 mg; contaminated with impurities believed to be derived from 8a).

$^1$H NMR (300 MHz, $d_6$-DMSO) δ8.16 (minor, d, 1H, J=7.8), 8.14 (major, d, 1H, J=7.8), 8.03 (major and minor, d, 1H, J=2.3), 7.81 (major and minor, d, 1H, J=2.3), 7.38 (major and minor, s, 1H), 7.31 (major and minor, d, 1H, J=2.4), 7.06 (major and minor, m, 2H), 6.83 (major, s, 1HO), 6.81 (minor, s, 1H), 6.32 (minor, d, 1H, J=7.7), 6.30 (major, d, 1H, J=7.7), 5.60 (major, d, 1H, J=7.5), 5.58 (minor, d, 1H, J=7.5), 5.49 (major and minor, m, 2H), 4.99 (major and minor, d, 2H, J=5.2), 4.82 (major, d, 2H, J=5.1), 4.75 (minor, d, 2H, J=5.2), 4.10 (major, dd, 1H, J=3.4, 9.6), 3.77 (minor, dd, 1H, J=3.6, 10.1), 3.58 (major and minor, dd, 1H, J=5.2, 7.9), 2.03–2.16 (major and minor, m, 5H), 1.66 (major and minor, s, 3H), 1.63 (major and minor, s, 3H), 1.35–1.55 (major and minor, m, 3H), 1.37 (major and minor, s, 3H), 1.29 (major and minor, s, 3H), 1.20 (major and minor, s, 3H), 1.14 (major and minor, s, 3H), 1.12 (major and minor, s, 3H), 0.99 (major and minor, s, 3H). When HPLC Method One was used, the elution time was 52.1 minutes.

Acid catalyzed removal of the acetonide protecting group from 9a

To a vial was added 240 mg (0.313 mmol) of 9a in 2 mL of $CD_3OD$/2 mL of THF (9a was not soluble in $CD_3OD$ alone) and 30 mL (0.03 mmol HCl; 10 mol %) of 1 N HCl(aq)(~1.7 mmol $H_2O$; ~5 equiv., not including $H_2O$ in $CD_3OD$ and THF). The reaction was monitored by TLC (1:1 EtOAc/hexanes) and HPLC (Method One) for one hour at room temperature. Both TLC and HPLC showed the formation of 5 and 5' (acetonide protecteed 6,7 dihydroxy bergamottin) as the predominant products. Trace amounts of 10 (~8 area %) were seen by HPLC. Column chromatography (35% EtOAc/65% hexanes) gave 23 mg of 5, 37 mg of 5' and 76 mg of recovered starting material 9a.

Alkylation of the free-phenol spiro-orthoester 7 with geranyl bromide

To a heat-gun dried vial and under a nitrogen atmosphere was added 15 mg (0.11 mmol; 1.7 equiv.) of $K_2CO_3$, 35 mg (0.063 mmol) of rac. 7 in 1 mL anhydrous THF and 25 mL (0.13 mmol; 2.0 equiv.) of geranyl bromide. The resulting slurry was heated to 50° C. for 24 hours.

The reaction mixture was subjected to column chromatography directly (2:1 hexanes/EtOAc, $R_f$~0.6) to give 15 mg (34% yield) of 11 as a pale yellow oil. Geranyl chloride can be used instead of the bromide.

$^1$H NMR (300 MHz, $CDCl_3$) δ8.15 (minor, d, 1H, J=9.8), 8.13 (major, d, 1H, J=9.8), 7.58 (major and minor, d, 1H, J=2.4), 7.42 (major and minor, d, 1H, J=2.4), 7.23 (major and minor, s, 1H), 7.15 (major and minor, s, 1H), 6.93 (minor, d, 1H, J=2.5), 6.91 (major, d, 1H, J=2.5), 6.80 (major and minor, m, 2H), 6.27 (minor, d, 1H, J=9.8), 6.25 (major, d, 1H, J=9.8), 6.59 (major and minor, m, 3H), 5.29 (major and minor, m, 1H), 4.93 (major and minor, d, 2H, J=6.9), 4.77 (major and minor, d, 2H, J=6.9), 4.19 (major, dd, 1H, J=3.3, 9.7), 3.80 (minor, dd, 1H, J=3.1, 10.1), 2.26 (major and minor, m, 1H), 1.90–2.06 (major and minor, m, 5H), 1.71 (major and minor, s, 3H), 1.69 (major and minor, s, 3H), 1.66 (major and minor, s, 3H), 1.53–1.66 (major and minor, m, 2H), 1.47 (major and minor, s, 3H), 1.26 (major and minor, s, 3H), 1.20 (major and minor, s, 3H). When HPLC Method One was used, the elution time was 53.1 minutes.

Silyl protected diethoxy-orthoesters 4c, 4d, 4e

A variety of silyl-protected diethoxy-orthoester is obtained following the procedure outlined for the synthesis of TBDMS-protected diethoxy-orthoester.

To a flask under a nitrogen atmosphere is added the silyl-protected bergaptol 3c (P=TIPS), 3d (P=TPBPS) or 3e (P=THDMF) and 2 equiv. of 1 M [$Et_3O$]$PF_6$ in $CH_2Cl_2$. After stirring at room temperature for 16 hours, the reaction is cooled to 0° C. and is added dropwise to 2.0 equiv. of NaOEt/EtOH solution at 0° C. Following the addition the reaction is stirred at 0° C. for 30 minutes and then poured into a 95:5 EtOAc/$NEt_3$ solution. The organic phase is rinsed with sat. NaCl. After in vacuo concentration to about $\frac{1}{10}$ of the original volume, the organic solution is loaded onto a plug of activated basic alumina. Elution with a 5:10:85 $NEt_3$/EtOAc/heptane solution followed by solvent removal gives the dialkoxy-orthoester.

Spiro-ortho Ester Synthesis 6c, 6d, 6e

Similarly, these silyl-protected diethoxy-orthoesters can be converted to the corresponding spiro-orthoester. These sterically more hindered silyl-protecting group may offer the added advantage of being more stable in the reaction mixture (de-silylation was observed as a side-reaction when R=TBDMS; this is at least partially responsible for the lower yield obtained compared with R=Bn). A THF solution of 4c, 4d or 4e is added to a solution containing 10 mol % PyTsOH and 1.1 equiv. of (R)-5. The reaction is monitored by TLC until the complete disappearance of 4c, 4d or 4e. The crude reaction mixture is then poured into EtOAc, rinsed with sat. $NaHCO_3$, dried with $Na_2SO_4$ and stripped of solvent. Column chromatography on $NEt_3$-deactivated silica gel gives the desired spiro-orthoester.

Deprotection of Silyl-protected Spiro-orthoesters 6c–e

Standard TBAF deprotection gives the free-phenol spiro-orthoester 7. A THF solution of 6c, 6d or 6e is treated with 1.0 equiv. of 1 M TBAF in THF at room temperature until the disappearance of the starting material. The crude is poured into EtOAc, rinsed with sat. NaCl, dried with $Na_2SO_4$ and stripped of solvent. Column chromatography (2:1 hexanes/EtOAc) gives the desired free-phenol spiro-orthoester.

Synthesis of Silyl Protected 6,7-dihydroxygeranyl Bromide 8b

This synthesis can be accomplished using the known precursors 12 with a variety of protecting groups (e.g. R=acetyl, benzyl, benzoyl, carbamoyl etc.). In general, base labile protecting groups can be utilized for this transformation. The examples will be given for an acetyl protected derivative. The use and versatility of the cyclic silylene protecting group is described in: B. M. Trost, C. G. Caldwell, E. Murayama and D. Heissler *J. Org. Chem.* 48, 3252(1983).

6,7-dihydroxygeranyl acetate is dissolved in acetonitrile, triethylamine is added followed by di-tert.butyldichlorosilane. The mixture is warmed to 65° C. until the reaction is complete. MTBE and water are added, the phases are separated and the organic layer dried over sodium sulfate. After removal of the solvent the silyl protected diol derivative is isolated. Conversion into the bromide is analogous to the acetonide procedure described above if a base labile protecting group is used. Since the cyclic silylene can be base sensitive the acetyl protecting group is preferred because it can be removed by treatment with methanolic potassium carbonate solution at room temperature. Once the primary alcohol is generated, reaction with phosphorus(III)bromide generates the desired bromide 8b.

Alkylation of 7 with Silyl Protected Side-chain 8b

To a THF solution of 7 is added 1.0 equiv. of $NEt_3$, 3.0 equiv. of $K_2CO_3$ and 2.0 equiv. of 8b. The resulting slurry is heated at 50° C. for 24 hours. The crude reaction mixture is poured into EtOAc, rinsed with sat. NaCl, dried with $Na_2SO_4$ and stripped of solvent. Column chromatography gives the desired diol-protected spiro-orthoester.

Deprotection of 9b

Treatment of 9b under standard TBAF de-silylation reactions gives the target molecule 10. To a THF solution of 9b is added 1.0–2.0 equiv. of 1 M TBAF in THF. Solid $K_2CO_3$ is added to ensure a non-acidic reaction medium. The reaction is carried out at room temperature and is monitored by TLC and HPLC until the complete disappearance of 9b. Standard aqueous work-up followed by column chromatography (if necessary) gives the desired target molecule 10.

Asymmetric Dihydroxylation of Alkene Spiro-orthoester 11

Alternatively, the desired target 10 can be obtained via the Sharpless AD of the olefinic substrate 11. To 11 in a 1:1 t-BuOH/$H_2O$ solution at 0° C. is added AD-Mix-β (1.4 g AD-Mix-β per mmol of 11) and 1.0 equiv. $MeSO_2NH_2$. The resulting slurry is stirred at 0° C. overnight and then quenched with 2 equiv. of $Na_2SO_3$. The crude aqueous reaction mixture is extracted with EtOAc. The EtOAc layer is then rinsed with 2N NaOH to remove the $MeSO_2NH_2$. The organic layer is dried over $Na_2SO_4$, filtered and stripped of solvent. The final product is purified via column chromatography, if necessary. Previous experiences (i.e. the conversion of 3f to 5) have shown that the Sharpless AD is regio-and chemo-selective (i.e. will only dihydroxylate the 6,7-olefin) and that the AD-Mix-β (AD-Mix-α is also commercially available) gives the desired (R) absolute configuration at C-6 of the side chain in high enantioselectivity. The enantioselectivity of the reaction can be ascertained via the hydrolysis of the spiro-orthoester 10 to the corresponding 6,7-dihydroxybergamottin monomers 5. AD-Mix-β is basic and therefore we do not need to be concerned about the possibility of the acid-catalyzed cleavage of the spiro-orthoester moiety.

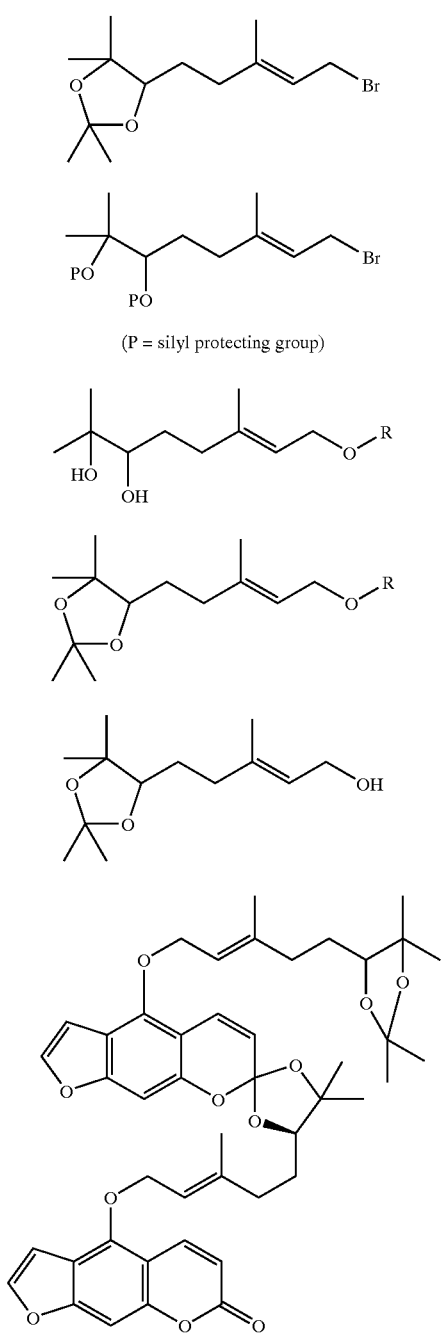

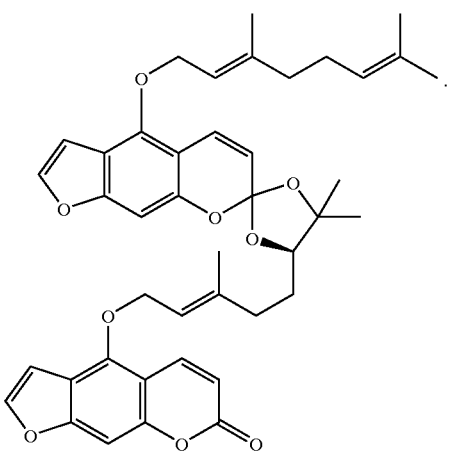

What is claimed is:

1. A process for the synthesis of an ortho ester or ortho carbonate comprising reacting an ester or carbonate with an agent that comprises a tri $C_{1-20}$ alkyl oxonium ion and a non-coordinating anion other than $[Et_3O][BF_4]$.

2. The process of claim 1, wherein the process is a process for producing an ortho ester and the ester is a cyclic ester.

3. The process of claim 1, wherein the process is a process for producing an ortho carbonate and the carbonate is a cyclic carbonate.

4. The process of claim 1, where the anion is not $[BF_4]$.

5. A process for the synthesis of an ortho ester or ortho carbonate from a hydroxy functionalized ester comprising reacting the hydroxy functionalized ester with a protecting group to form a protected hydroxyl ester, followed by reacting said protected hydroxyl ester with an agent, wherein said agent comprises a tri $C_{1-20}$ alkyl oxonium ion and a non-coordinating anion and does not comprise $[Et_3O][BF_4]$.

6. The process of claim 5, wherein the process is a process for producing an ortho ester and the ester is a cyclic ester.

7. The process of claim 5, wherein the process is a process for producing an ortho carbonate and the carbonate is a cyclic carbonate.

8. The process as claimed in claim 5, further comprising reacting the protected ortho ester or carbonate with a nucleophile.

9. The process of claim 5, wherein said nucleophile is selected from the group consisting of LiOMe, NaOMe, KOMe, CsOMe, LiOEt, NaOEt, KOEt, NaOn-Pr, NaOn-Bu, NaOBn, NaOCH$_2$CH$_2$ONe; and mixtures thereof.

10. The process of claim 8, wherein said nucleophile is a $C_{1-20}$ alkoxide.

11. A process for the synthesis of an orthoester or orthocarbonate comprising:
reacting an ester or carbonate with a trialkyloxonium alkylating agent comprising a non-coordinating anion to form an alkylated ester cation or alkylated carbonate cation, and
reacting the alkylated ester cation or alkylated carbonate cation with an alkoxide salt to form the orthoester or orthocarbonate.

12. The process of claim 11 wherein the trialkyloxonium alkylating agent is triethyloxonium hexafluorophosphate.

13. The process of claim 11 wherein the alkoxide salt is an alkali metal salt of an alcohol selected from the group consisting of methanol, ethanol, n-propanol, n-butanol, benzyl alcohol, ethylene glycol; and mixtures thereof.

14. The process of claim 11 wherein the process is for the synthesis of an orthoester, the ester is a lactone and the orthoester is a cyclic orthoester.

15. The process of claim 11 wherein the process is a process for producing an orthocarbonate, the carbonate is a cyclic carbonate and the orthocarbonate is a cyclic orthocarbonate.

16. A process for synthesis of an ortho ester of a hydroxyl-functionalized ester comprising:

reacting the hydroxyl-functionalized ester with a hydroxyl-protecting reagent to form a protected-hydroxyl functionalized ester, reacting the protected-hydroxyl-functionalized ester with a trialkyloxonium alkylating agent comprising a non-coordinating anion to form a protected-hydroxyl-functionalized alkylated ester cation, reacting the protected-hydroxyl-fuctionalized alkylated ester cation with an alkoxide salt to form a protected-hydroxyl-functionalized ortho ester, and, deprotecting the protected-hydroxyl-fuctionalized ortho ester to form the ortho ester of the hydroxyl-functionalized ester.

17. The process of claim 16 wherein the hydroxyl-functionalized ester is a hydroxyl-functionalized lactone and the ortho ester of the hydroxyl-fuctionalized ester is a cyclic ortho ester.

18. A process for the synthesis of a spiro orthoester comprising:

reacting a lactone with a trialkyloxonium alkylating agent comprising a non-coordinating anion to form an alkylated lactone cation, reacting the alkylated lactone cation with an alkoxide salt to form a cyclic orthoester, and reacting the cyclic orthoester with a diol to form the spiro orthoester.

19. A process for synthesis of a spiro ortho ester of a hydroxyl-functionalized lactone comprising:

reacting the hydroxyl-functionalized lactone with a hydroxyl-protecting reagent to form a protected-hydroxyl functionalized lactone, reacting the protected-hydroxyl-fuctionalized lactone with a trialkyloxonium alkylating agent comprising a non-coordinating anion to form a protected-hydroxyl-functionalized alkylated lactone cation, reacting the protected-hydroxyl-fuctionalized alkylated lactone cation with an alkoxide salt to form protected-hydroxyl-fuctionalized cyclic ortho ester, reacting the protected-hydroxyl-fuctionalized cyclic ortho ester with a diol to form a protected-hydroxyl-fuctionalized spiro ortho ester, and deprotecting the protected-hydroxyl-fuctionalized spiro ortho ester to form the spiro ortho ester of the hydroxyl-functionalized lactone.

* * * * *